US010139362B2

(12) United States Patent
Ohgami et al.

(10) Patent No.: US 10,139,362 B2
(45) Date of Patent: Nov. 27, 2018

(54) SENSOR HEAD, ELECTROCHEMICAL SENSOR, AND METHOD FOR USING ELECTROCHEMICAL SENSOR

(75) Inventors: Naoto Ohgami, Kyoto (JP); Hideyuki Yamashita, Kyoto (JP); Yutaro Okuno, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 1102 days.

(21) Appl. No.: 14/236,860

(22) PCT Filed: Apr. 25, 2012

(86) PCT No.: PCT/JP2012/061052
§ 371 (c)(1),
(2), (4) Date: Apr. 2, 2014

(87) PCT Pub. No.: WO2013/018406
PCT Pub. Date: Feb. 7, 2013

(65) Prior Publication Data
US 2014/0209485 A1  Jul. 31, 2014

(30) Foreign Application Priority Data

Aug. 1, 2011  (JP) ................. 2011-168619

(51) Int. Cl.
*G01N 27/333*  (2006.01)
*G01N 27/327*  (2006.01)

(52) U.S. Cl.
CPC ....... *G01N 27/333* (2013.01); *G01N 27/3272* (2013.01)

(58) Field of Classification Search
CPC ............ G01N 27/333; G01N 27/3272; G01N 27/4166; G01N 27/4167; G01N 27/301;
(Continued)

(56) References Cited

U.S. PATENT DOCUMENTS 4,872,966 A * 10/1989 Kotani ................. G01N 27/333
204/414
5,234,568 A * 8/1993 Tomita ................. G01N 27/307
204/406
(Continued)

FOREIGN PATENT DOCUMENTS

CN  101454667 A  6/2009
EP  0 282 349 A2  9/1988
(Continued)

OTHER PUBLICATIONS

Oct. 13, 2014 Office Action issued in Chinese Application No. 201280038376.0.
(Continued)

*Primary Examiner* — Gurpreet Kaur
(74) *Attorney, Agent, or Firm* — Oliff PLC

(57) ABSTRACT

There is provided a sensor head which includes a mounting surface having insulation property. A first electrode and a second electrode are arranged on the mounting surface in a spaced-apart manner from each other. A liquid retaining material is arranged on the mounting surface in a state where the liquid retaining material covers the first electrode and the second electrode integrally. The liquid retaining material is impregnated with a standard liquid which is used as a reference in the electrochemical measurement.

8 Claims, 17 Drawing Sheets

(58) Field of Classification Search
CPC ............. G01N 27/302; G01N 27/4117; G01N 27/4035
See application file for complete search history.

(56) References Cited

U.S. PATENT DOCUMENTS

| | | | | |
|---|---|---|---|---|
| 5,248,403 | A * | 9/1993 | Tomita | ............... G01N 27/307 204/409 |
| 5,393,391 | A * | 2/1995 | Dietze | ............... G01N 27/4035 204/409 |
| 2002/0027074 | A1* | 3/2002 | Tominaga | ............. G01N 27/40 204/414 |
| 2004/0004014 | A1* | 1/2004 | Grossman | ............ A61F 15/002 206/440 |
| 2006/0127964 | A1* | 6/2006 | Ford | ................. A61B 5/14532 435/14 |

FOREIGN PATENT DOCUMENTS

| JP | A-59-190653 | 10/1984 |
|---|---|---|
| JP | U-63-96455 | 6/1988 |
| JP | A-63-289444 | 11/1988 |
| JP | A-3-100452 | 4/1991 |
| JP | A-2003-344346 | 12/2003 |
| JP | A-2009-150902 | 7/2009 |

OTHER PUBLICATIONS

International Search Report issued in International Patent Application No. PCT/JP2012/061052 dated Aug. 7, 2012.
Written Opinion of the International Searching Authority issued in International Patent Application No. PCT/JP2012/061052 dated Aug. 7, 2012.
Jul. 21, 2015 Office Action Issued in Japanese Patent Application No. 2011-168619.
Jul. 1, 2015 Second Office Action issued in Chinese Patent Application No. 201280038376.0.

* cited by examiner

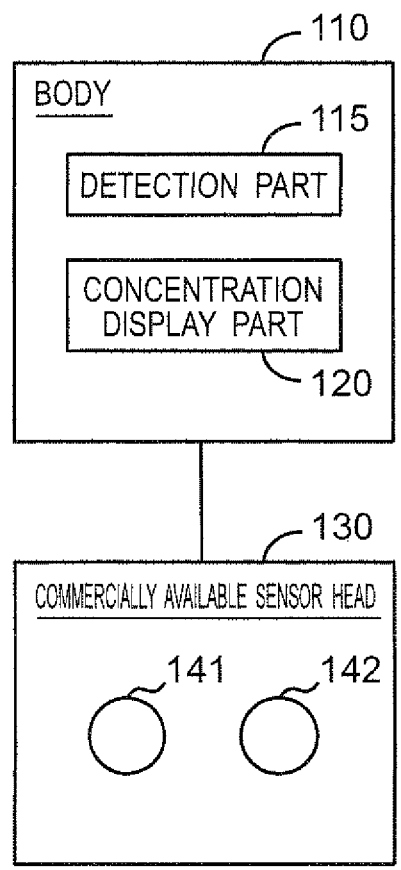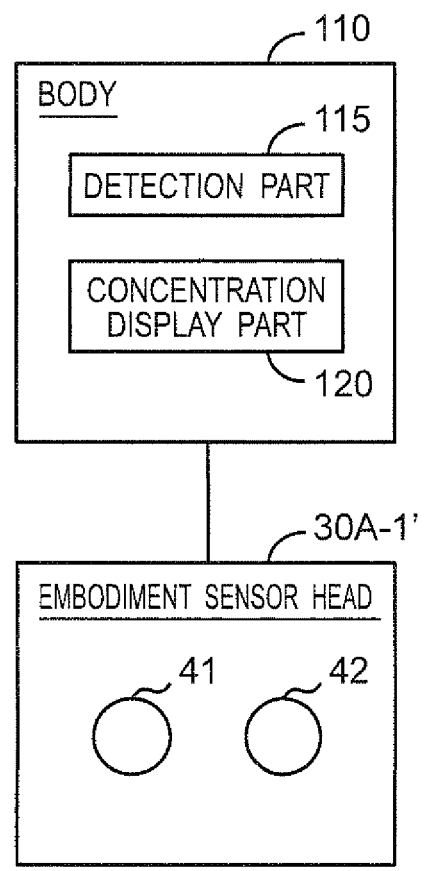

|  | | DIRECT SPRAYING | | IMMERSION MEASUREMENT |
| --- | --- | --- | --- | --- |
|  | | (A) WITH LIQUID RETAINING SHEET | (B) WITHOUT LIQUID RETAINING SHEET | (C) WITHOUT LIQUID RETAINING SHEET |
| STABILITY σ OF DETECTED POTENTIAL DIFFERENCE [mV] | PERIOD OP1 | 1.06 | 6.02 | 0.29 |
|  | PERIOD OP2 | 0.44 | 2.60 | 0.23 |
| 90% RESPONSE TIME [sec] | | 29 | NOT MEASURED | 25 |

SENSOR HEAD, ELECTROCHEMICAL SENSOR, AND METHOD FOR USING ELECTROCHEMICAL SENSOR

TECHNICAL FIELD

The present invention relates to a sensor head, and more particularly to a sensor head for performing electrochemical measurement.

The present invention also relates to an electrochemical sensor provided with such a sensor head.

The present invention further relates to a method for using an electrochemical sensor which uses such an electrochemical sensor.

BACKGROUND ART

Conventionally, as an electrochemical sensor, for example, a compact sodium ion meter C-122 and a compact nitric acid ion meter B-343 both of which are manufactured by HORIBA, Ltd. and the like have been commercially available. When a user intends to perform measurement using such an electrochemical sensor, the electrochemical sensor is calibrated using standard liquids for calibration in advance for ensuring accuracy in measurement.

For example, when the compact sodium ion meter C-122 is calibrated in accordance with one-liquid calibration, calibration is performed in accordance with the following steps. (1) The sensor (meaning a sensor head, this definition used hereinafter) is cleanly washed using a cleaning liquid, and the cleaning liquid is wiped away using dry tissue paper or the like. This cleaning operation is repeated a few times. (2) A sampling sheet is placed on the sensor, and an STD standard solution (first standard solution) is dropped on the sampling sheet (may be directly dropped on the sensor). (3) After the sensor becomes stable, a display of the sensor is adjusted to 20×100 by an STD volume. (4) The sensor is cleaned using a cleaning liquid and, thereafter, the cleaning liquid is wiped out by dry tissue paper or the like (calibration finished).

When the compact sodium ion meter C-122 is calibrated in accordance with two-liquid calibration, calibration requires an operation where an SLOPE standard liquid (second standard liquid) is additionally used, and a display of the sensor is adjusted to 15×10 by a SLOPE volume.

The same calibration steps are performed also with respect to calibration of the compact nitric acid ion meter B-343.

Such calibration is extremely cumbersome for users in general and there also is a possibility that an error will occur during the operation.

In view of the above, conventionally, as described in Japanese Patent Laid-open Publication No. 2009-150902, there has been proposed a device where a spike is mounted on a sample holding chamber in the inside of a cartridge to be inserted into a reading device, a package (a foiled pack filled with a standard liquid for calibration) is broken by the spike when a user inserts the cartridge into the reading device, and a liquid is introduced into a conduit from the sample holding chamber. With the use of such a device, the user can perform calibration automatically by merely inserting the cartridge into the reading device even when the user does not perform the operations for calibration intentionally.

PRIOR ART DOCUMENTS

Patent Documents

Patent Document 1: Japanese Patent Laid-open Publication No. 2009-150902

SUMMARY OF THE INVENTION

Problems to be Solved by the Invention

However, the device disclosed in the patent document (Japanese Patent Laid-open Publication No. 2009-150902) has the following drawbacks. That is, the device includes the conduit which extends from the sample holding chamber and a pump for supplying a liquid through the conduit and hence, the device becomes large-sized and pushes up a cost.

Accordingly, it is an object of the present invention to provide a sensor head for performing electrochemical measurement which enables a user to perform calibration with a simple operation and which can be miniaturized as well as be manufactured at a low cost.

It is another object of the present invention to provide an electrochemical sensor which includes such a sensor head, and enables a user to perform calibration with a simple operation and which can be miniaturized as well as be manufactured at a low cost.

It is still another object of the present invention to provide a method for using an electrochemical sensor, like such an electrochemical sensor above described, enabling a user to perform measurement easily.

Solutions to the Problems

To solve the above-mentioned problems, a sensor head for performing electrochemical measurement according to the present invention, comprises:

a mounting surface having insulation property;

a first electrode and a second electrode arranged on the mounting surface in a spaced-apart manner from each other; and a liquid retaining material arranged on the mounting surface in a state where the liquid retaining material covers the first electrode and the second electrode integrally, wherein the liquid retaining material is impregnated with a standard liquid which is used as a reference in the electrochemical measurement.

In the present specification, "electrochemical measurement" means measurement where the electric signal is detected using a converting element having a function of generating an electric signal (an electric current, a voltage, a quantity of electricity or a change in the electric current or the voltage) corresponding to a property (concentration or the like) of an object to be measured, and the electric signal is converted into a quantity indicative of the property of the object to be measured.

In the present specification, "insulation property" means electric insulation property.

In the present specification, "liquid retaining" means a property of retaining a liquid such as water or an aqueous solution in an impregnated state.

In the present specification, "impregnated" means that a liquid is contained in gaps formed in constitution of the liquid retaining material or in structure of the liquid retaining material. When the liquid retaining material is in direct contact with the electrodes, for example, the liquid exudes from the liquid retaining material so that there arises a state where the liquid is brought into contact with the electrodes.

In the sensor head of the present invention, the liquid retaining material is arranged so as to cover the first electrode and the second electrode on the mounting surface integrally. The liquid retaining material is impregnated with a standard liquid which is used as a reference in electrochemical measurement. Accordingly, by detecting a potential difference or an electric current between the first electrode and the second electrode in a state where the standard liquid exudes from the liquid retaining material sc that the standard liquid is brought into contact with the first electrode and the second electrode, it is possible to obtain measured data (potential difference or electric current, the same definition being applicable hereinafter) with respect to the standard liquid. Accordingly, by detecting a potential difference or an electric current between the first electrode and the second electrode under a condition that the sensor head is mounted on the sensor body, for example, a user can perform calibration of the sensor head without intentionally performing an operation for calibration. After obtaining measured data with respect to the standard liquid, the user brings the sensor head into a state where the standard liquid in the liquid retaining material is replaced with a liquid to be measured by spraying the liquid to be measured to the liquid retaining material or by immersing the liquid retaining material into the liquid to be measured. By detecting a potential difference or an electric current between the first electrode and the second electrode in such a state, it is possible to obtain measured data (potential difference or electric current, the same definition being applicable hereinafter) with respect to the liquid to be measured. By calibrating the measured data with respect to the liquid to be measured using the measured data with respect to the standard liquid, it is possible to obtain measured electrochemical data with respect to the liquid to be measured with high degree of accuracy.

The sensor head is substantially configured such that the liquid retaining material impregnated with the standard liquid is arranged so as to cover the first electrode and the second electrode on the mounting surface integrally. Accordingly, it is possible to miniaturize the sensor head and to manufacture the sensor head at a low cost.

In the present specification, "spraying a liquid to be measured to the liquid retaining material" includes the case where a liquid to be measured which is discharged from a living body is directly sprayed to the liquid retaining material from the living body, and the case where a fixed amount of liquid to be measured is dropped on the liquid retaining material using an instrument such as a micro pipet.

In the present specification, "immersing the liquid retaining material into a liquid to be measured" includes the case where not only the liquid retaining material but also a portion of the sensor head (particularly the mounting surface) where the liquid retaining material is arranged are immersed into the liquid to be measured together with the liquid retaining material.

In the sensor head according to one embodiment, the liquid retaining material is provided in form of a sheet, and the liquid retaining material has liquid permeation property which allows a liquid to be measured to permeate the liquid retaining material provided in form of a sheet toward the first electrode and the second electrode.

In the sensor head according to this embodiment, the liquid retaining material is provided in form of a sheet. Accordingly, the sensor head can be formed with a small thickness. The liquid retaining material has a liquid permeation property which allows a liquid to be measured to permeate the liquid retaining material provided in form of a sheet toward the first electrode and the second electrode. Accordingly, a user can easily bring the sensor head into a state where a standard liquid in a liquid retaining material is replaced with a liquid to be measured by spraying the liquid to be measured to the liquid retaining material or by immersing the liquid retaining material into the liquid to be measured.

The sensor head according to one embodiment further comprises a sealing member which covers at least the liquid retaining material for preventing a change in the standard liquid impregnated into the liquid retaining material.

In the present specification, "a change in the standard liquid" means a change in drying or concentration due to evaporation, oxidation due to contact of the standard liquid with air or the like.

The sensor head according to this embodiment includes the sealing member which covers at least the liquid retaining material. Due to such a sealing member, a change in the standard liquid impregnated into the liquid retaining material can be prevented. Accordingly, calibration with high degree of accuracy can be realized. This brings about an advantageous effect that, for example, when the sensor head is placed on a market as a commercially available product, it is possible to ensure a long period during which the sensor head can be calibrated with high degree of accuracy using the standard liquid. It is desirable that the sealing member be removed by a user immediately before the sensor head is used.

In the sensor head according to one embodiment, the sealing member is provided in form of a sheet having a planar-direction size larger than a planar-direction size of the liquid retaining material, and an edge portion of the sealing member in form of a sheet is hermetically adhered to the mounting surface.

In the present specification, "planar-direction size" means a size in the direction along the mounting surface.

In the sensor head according to this embodiment, the sealing member is provided in form of a sheet having a planar-direction size larger than a planar-direction size of the liquid retaining material. Accordingly, the sensor head can be constituted with a small thickness. Further, the edge portion of the sealing member in form of a sheet is hermetically adhered to the mounting surface and hence, a change in the standard liquid can be prevented with certainty.

In the sensor head according to one embodiment, the sealing member is provided in form of a bag, and the sealing member covers a whole or a portion of the substrate forming the mounting surface together with the first electrode, the second electrode and the liquid retaining material.

In the sensor head according to this embodiment, the sealing member is provided in form of a bag. Accordingly, the reduction in thickness of the sensor head is not obstructed by the sealing member. Further, the sealing member covers a whole or a portion of the substrate forming the mounting surface together with the first electrode, the second electrode and the liquid retaining material and hence, the evaporation of the standard liquid can be prevented with certainty.

The sensor head according to one embodiment further comprises a liquid blocking film which blocks permeation of the liquid, the liquid blocking film being arranged between the liquid retaining material and the first and the second electrodes.

The sensor head according to this embodiment further comprises a liquid blocking film which blocks permeation of the liquid, the liquid blocking film being arranged between the liquid retaining material and the first and the second electrodes. Accordingly, it is possible to prevent a drawback that the standard liquid impregnated into the liquid retaining material is deteriorated due to a contact with the first electrode and the second electrode over a long period. This brings about an advantageous effect that, for example, when the sensor head is placed on a market as a commercially available product, it is possible to ensure a long period during which the sensor head can be calibrated with high degree of accuracy using the standard liquid. It is desirable that the liquid blocking film is removed by a user immediately before the sensor head is used.

Particularly, when the first electrode and the second electrode are configured to contain inner liquids (described later) for ion concentration measurement, the standard liquid impregnated into the liquid retaining material and these inner liquids are blocked from each other by the liquid blocking film and hence, the standard liquid impregnated into the liquid retaining material and these inner liquids are not mixed with each other. Accordingly, it is possible to adopt the inner liquids and the standard liquid optimum for the first electrode and the second electrode without taking into account the mixing of liquids with each other.

In the sensor head according to one embodiment, the liquid blocking film has a projecting portion which projects in one direction from a region where the liquid retaining material is present such that the liquid blocking film is capable of being pulled in the one direction along the mounting surface between the liquid retaining material and the first and the second electrodes, while the liquid retaining material includes an extending portion which goes beyond the liquid blocking film and extends in a direction opposite to the one direction, and the extending portion is hermetically adhered to the mounting surface.

In the sensor head of this embodiment, the liquid blocking film includes the projecting portion which projects in the one direction from the region where the liquid retaining material is present. Accordingly, immediately before using the sensor head, the user pinches the projecting portion of the liquid blocking film with his fingers, and pulls out the liquid blocking film from between the liquid retaining material and the first and the second electrodes along the mounting surface. On the other hand, the liquid retaining material has an extending portion which extends in the direction opposite to the one direction while extending beyond the liquid blocking film, and the extending portion is hermetically adhered to the mounting surface. Accordingly, when the liquid blocking film is pulled out in the one direction, the liquid retaining material is not removed together with the liquid blocking film and is brought into direct contact with the first electrode and the second electrode. Accordingly, there arises a state where the standard liquid exudes from the liquid retaining material and is brought into contact with the first electrode and the second electrode. By detecting a potential difference or an electric current between the first electrode and the second electrode in this state, the measured data with respect to the standard liquid can be obtained with high degree of accuracy. Then, calibration is performed using the measured data with respect to the standard liquid.

In the sensor head according to one embodiment, the projecting portion of the liquid blocking film is joined to the sealing member.

In the sensor head according to this embodiment, the projecting portion of the liquid blocking film is joined to the sealing member. Accordingly, in removing the sealing member immediately before a user uses the sensor head, the user is aware of the joining of the sealing member with the liquid blocking film by way of the projecting portion and is advised to pull out the liquid blocking film. By pinching the sealing member with his fingers and by pulling the sealing member in one direction along the mounting surface, the user can pull out the liquid blocking film in the one direction from between the liquid retaining material and the first and the second electrodes by way of the projecting portion. That is, by performing an operation of removing the sealing member one time, the user can pull out the liquid blocking film simultaneously. In this case, it is possible to prevent the user from forgetting to pull out the liquid blocking film.

In the sensor head according to one embodiment, the liquid retaining material is brought into direct contact with the first electrode and the second electrode.

In the sensor head according to this embodiment, the liquid retaining material is brought into direct contact with the first electrode and the second electrode. Accordingly, at a point of time that a user intends to use the sensor head, the sensor head is already brought into a state where the standard liquid exudes from the liquid retaining material and is brought into contact with the first electrode and the second electrode. By detecting a potential difference or an electric current between the first electrode and the second electrode in such a state, it is possible to readily obtain measured data with respect to the standard liquid.

In the sensor head according to one embodiment, the liquid retaining material is in a gel state.

In the sensor head according to this embodiment, the liquid retaining material is in a gel state. Therefore, various materials such as agar, gelatin, agarose gel, cellulose gel or polyacrylamide, for example, can be adopted as the liquid retaining material.

In the sensor head according to one embodiment, the liquid retaining material is an aggregate of fibers in cloth form or in paper form.

In the sensor head according to this embodiment, the liquid retaining material is an aggregate of fibers in cloth form or in paper form. Therefore, various materials such as filter paper, Kimwipe (trademark owned by NIPPON PAPER CRECIA Co., LTD.) or a filter can be adopted as the liquid retaining material.

In the sensor head according to one embodiment, the liquid retaining material is a porous material.

In the sensor head according to this embodiment, the liquid retaining material is a porous material. Therefore, various materials such as a sponge can be adopted.

In the sensor head according to one embodiment, the liquid retaining material has resistance to the standard liquid.

In the present specification, "resistance" against the standard liquid means a property that the liquid retaining material is not changed physically or chemically even when the liquid retaining material is brought into contact with the standard liquid thus maintaining an original state.

In the sensor head according to this embodiment, the liquid retaining material has resistance to the standard liquid. Accordingly, the sensor head can maintain a state where the standard liquid is impregnated into the liquid retaining material over a long period. This advantageous effect is particularly remarkable when the sensor head is placed on a market as a commercially available product, for example.

In the sensor head according to one embodiment, the first electrode is constituted of a first core material having electric conductivity, and an ion selection film which is mounted on a surface of the first core material in a contact manner and selectively allows specific ion species contained in an object to be measured to permeate therethrough or to be absorbed therein, and the second electrode is constituted of only a conductive material.

According to the sensor head of this embodiment, the concentration of specific ion species can be measured.

In the sensor head according to one embodiment, the first electrode is constituted of a first core material having electric conductivity, and a first ion selection film which is mounted on a surface of the first core material in a contact manner, the second electrode is constituted of a second core material having electric conductivity, and a second ion selection film which is mounted on a surface of the second core material in a contact manner, and the first ion selection film and the second ion selection film selectively allow ion species different from each other and contained in an object to be measured to permeate therethrough or to be absorbed therein.

According to the sensor head of this embodiment, a concentration ratio between ion species different from each other can be measured.

In the sensor head according to one embodiment, the first electrode includes a first core material having electric conductivity, a first envelope surrounding the first core material and having insulation property, and a first inner liquid for measurement of ion concentration which is filled between the first envelope and the first core material, the second electrode includes a second core material having electric conductivity, a second envelope surrounding the second core material and having insulation property, and a second inner liquid for measurement of ion concentration which is filled between the second envelope and the second core material, and a first window portion and a second window portion which are capable of allowing a contact between the first inner liquid, the second inner liquid and the standard liquid or the liquid to be measured are respectively formed on a surface of the first envelope and a surface of the second envelope which face the liquid, retaining material in an opposed manner.

According to the sensor head of this embodiment, the first electrode contains the first inner liquid filled between the first envelope and the first core material for ion concentration measurement, and the second electrode contains the second inner liquid filled between the second envelope and the second core material for ion concentration measurement. A contact between the first inner liquid, the second inner liquid and the standard liquid or the liquid to be measured is allowed through the first window portion and the second window portion. As a result, the sensor head for electrochemical measurement which can measure various ion species is constituted by selectively setting various materials as the first inner liquid and the second inner liquid.

In the sensor head according to one embodiment, the first inner liquid and the second inner liquid are respectively same as the standard liquid in content.

In the sensor head according to this embodiment, the first inner liquid and the second inner liquid are respectively same as the standard liquid in content. Accordingly, even when the mixture of the first inner liquid, the second inner liquid and the standard liquid occurs through the first window portion and the second window portion respectively, no change occurs ire the compositions of the first inner liquid, the second inner liquid or the standard liquid. Accordingly, calibration with high degree of accuracy can be realized. Further, this brings about an advantageous effect that, for example, when the sensor head is placed on a market as a commercially available product, it is possible to ensure a long period during which the sensor head can be calibrated with high degree of accuracy by the standard liquid.

In the sensor head according to one embodiment, an ion selection film which selectively allows a specific ion species contained in the liquid to be measured to permeate therethrough or to be absorbed therein is provided to the first window portion, and a liquid communication path which allows the communication flow between the standard liquid or the liquid to be measured and the second inner liquid is formed in the second window portion.

According to the sensor head of this embodiment, the concentration of the specific ion species can be measured.

In the sensor head according to one embodiment, a first ion selection film and a second ion selection film which selectively allow ion species different from each other and contained in the liquid to be measured to permeate therethrough or to be absorbed therein are provided to the first window portion and the second window portion, respectively.

According to the sensor head of this embodiment, a concentration ratio between ion species different from each other can be measured.

In the sensor head according to one embodiment, the mounting surface is one main surface of a substrate having a predetermined size, and a first pullout electrode and a second pullout electrode which respectively extend from the first and the second electrodes toward an edge portion of the substrate on the mounting surface are provided to the mounting surface.

In the sensor head according to this embodiment, a first pullout electrode and a second pullout electrode which respectively extend from the first and the second electrodes toward an edge portion of the substrate on the mounting surface are provided to the mounting surface. Accordingly, for example, a user mounts portions of the sensor head on which the first pullout electrode and the second pullout electrode extend (the portions being referred to as "electrode pad portions") on a connector having contacts corresponding to the first pullout electrode and the second pullout electrode. Thereby, a potential difference or an electric current between the first electrode and the second electrode can be easily detected by way of the connector. After measured electrochemical data with respect to a liquid to be measured is obtained, the sensor head can be easily removed from the connector. Accordingly, the sensor head is easily disposed of along with advantages that the sensor head can be miniaturized as well as be manufactured at a low cost.

An electrochemical sensor of the present invention comprises:

a sensor head according to the present invention; and a detection part which detects a potential difference or an electric current between the first electrode and the second electrode.

According to the electrochemical sensor of the present invention, the detection part detects a potential difference or an electric current between the first electrode and the second electrode in the sensor head, in a state where the standard liquid exudes from the liquid retaining material so that the standard liquid is brought into contact with the first electrode and the second electrode. Thereby, it is possible to obtain measured data with respect to the standard liquid. Accordingly, by detecting a potential difference or an electric current between the first electrode and the second electrode under a condition that the sensor head is mounted on the sensor body, for example, a user can perform calibration of the sensor head without intentionally performing an operation for calibration. After obtaining measured data with respect to the standard liquid, the user brings the sensor head into a state where the standard liquid in the liquid retaining material is replaced with a liquid to be measured by spraying the liquid to be measured to the liquid retaining material or by immersing the liquid retaining material into the liquid to be measured. By detecting a potential difference or an electric current between the first electrode and the second electrode by the detection part in such a state, it is possible to obtain measured data with respect to the liquid to be measured. By calibrating the measured data with respect to the liquid to be measured using the measured data with respect to the standard liquid, it is possible to obtain measured electrochemical data with respect to the liquid to be measured with high degree of accuracy.

Further, since the sensor head can be miniaturized and can be manufactured at a low cost, the electrochemical sensor can be miniaturized and can be manufactured at a low cost as the whole.

In another aspect, an electrochemical sensor according to the present invention, comprises:

a sensor head according to the present invention, wherein the mounting surface is one main surface of a substrate having a predetermined size, and a first pullout electrode and a second pullout electrode which extend toward an edge portion of the substrate from the first electrode and the second electrode are provided on the mounting surface;

a body which includes a connector on which electrode pad portions where the first pullout electrode and the second pullout electrode of the sensor head extend are detachably mounted; and a detection part mounted on the body, the detection part detecting a potential difference or an electric current between the first electrode and the second electrode by way of the first pullout electrode and the second pullout electrode of the sensor head mounted on the connector.

In the electrochemical sensor according to the present invention, in using the electrochemical sensor, the user mounts the electrode pad portion of the sensor head on the connector having contacts corresponding to the first pullout electrode and the second pullout electrode. Then, the detection part detects a potential difference or an electric current between the first electrode and the second electrode in the sensor head, in a state where the standard liquid exudes from the liquid retaining material so that the standard liquid is brought into contact with the first electrode and the second electrode. Thereby, it is possible to obtain measured data with respect to the standard liquid. Accordingly, by detecting a potential difference or an electric current between the first electrode and the second electrode under a condition that the sensor head is mounted on the sensor body, for example, a user can perform calibration of the sensor head without intentionally performing an operation for calibration. After obtaining measured data with respect to the standard liquid, the user brings the sensor head into a state where the standard liquid in the liquid retaining material is replaced with a liquid to be measured by spraying the liquid to be measured to the liquid retaining material or by immersing the liquid retaining material into the liquid to be measured. By detecting a potential difference or an electric current between the first electrode and the second electrode by the detection part in such a state, it is possible to obtain measured data with respect to the liquid to be measured. By calibrating the measured data with respect to the liquid to be measured using the measured data with respect to the standard liquid, it is possible to obtain measured electrochemical data with respect to the liquid to be measured with high degree of accuracy.

Here, the portion of the sensor head where the liquid retaining material is arranged can be configured to project outwardly from the body. In this case, a hand-hold-type electrochemical sensor which the user uses by holding the body with his hand may be provided. With the use of such a hand-hold-type electrochemical sensor, the user can easily perform an operation of spraying a liquid to be measured to the liquid retaining material, and an operation of immersing the liquid retaining material into a liquid to be measured.

The electrochemical sensor according to one embodiment, further comprises:

a first control part which performs a first control for detecting the potential difference or the electric current by operating the detection part with respect to the standard liquid;

a second control part which performs a second control for detecting the potential difference or the electric current by operating the detection part with respect to the liquid to be measured; and a third control part which outputs a signal indicative of measured electrochemical data of the liquid to be measured by performing an arithmetic operation using the concentration of a specific component of the standard liquid, the potential difference or the electric current detected with respect to the standard liquid, and the potential difference or the electric current detected with respect to the liquid to be measured.

In the electrochemical sensor of this embodiment, the first control part performs a first control for detecting the potential difference or the electric current by operating the detection part with respect to the standard liquid. The second control part performs a second control for detecting the potential difference or the electric current by operating the detection part with respect to the liquid to be measured. Then, the third control part outputs a signal indicative of measured electrochemical data of the liquid to be measured by performing an arithmetic operation using the concentration a specific component of the standard liquid, the potential difference or the electric current detected with respect to the standard liquid, and the potential difference or the electric current detected with respect to the liquid to be measured. Accordingly, it is possible to obtain the concentration of the specific component in the object to be measured.

In the electrochemical sensor according to one embodiment, the first control part starts the first control under a condition that the electrode pad portion of the sensor head is mounted on the connector, and the second control part starts the second control under a condition that a predetermined instruction is inputted after the first control is finished.

In the electrochemical sensor of this embodiment, the first control part starts the first control under a condition that the electrode pad portion of the sensor head is mounted on the connector. Therefore, a user can perform calibration of the sensor head without intentionally performing an operation for calibration. The second control part starts the second control under a condition that a predetermined instruction is inputted after the first control is finished. The predetermined instruction is made so as to operate the detection part in a state where the standard liquid in the liquid retaining material is replaced with the material to be measured. Thereby, the measured electrochemical data with respect to the liquid to be measured can be obtained with high degree of accuracy.

A method for using an electrochemical sensor according to the present invention uses an electrochemical sensor including a sensor head of the present invention wherein the liquid retaining material is directly in contact with the first and the second electrodes, and further including a detection part which detects a potential difference or an electric current between the first electrode and the second electrode, wherein the method comprising the steps of:

detecting the potential difference or the electric current with respect to the standard liquid by operating the detection part; and subsequently detecting the potential difference or the electric current with respect to the liquid to be measured by operating the detection part in a state where the standard liquid in the liquid retaining material is replaced with the liquid to be measured by spraying the liquid to be measured to the liquid retaining material or by immersing the liquid retaining material into the liquid to be measured.

In such a method for using an electrochemical sensor of the present invention, after the measured data with respect to the standard liquid is obtained, a user sprays the liquid to be measured to the liquid retaining material or immerses the liquid retaining material into the liquid to be measured. Thereby, the measured data with respect to the liquid to be measured is obtained. Accordingly, a user can perform measurement with a simple operation. Particularly, when a liquid to be measured discharged from a living body (urine, for example) is directly sprayed to the liquid retaining material from the living body, it is unnecessary for a user to prepare a container for storing the liquid to be measured or instrument for handling the liquid to be measured and hence, the method becomes convenient.

In another aspect, a method for using an electrochemical sensor according to the present invention uses an electrochemical sensor including a sensor head of the present invention which has a liquid blocking film arranged between the liquid retaining material and the first and the second electrodes for blocking permeation of liquid, and further including a detection part which detects a potential difference or an electric current between the first electrode and the second electrode, the method comprising the steps of:

detecting the potential difference or the electric current by operating the detection part with respect to the standard liquid by pulling out the liquid blocking film from between the liquid retaining material and the first and the second electrodes, thus bringing the liquid retaining material into contact with the first electrode and the second electrode, and subsequently detecting the potential difference or the electric current with respect to the liquid to be measured by operating the detection part in a state where the standard liquid in the liquid retaining material is replaced with the liquid to be measured by spraying the liquid to be measured to the liquid retaining material or by immersing the liquid retaining material into the liquid to be measured.

In the method of using an electrochemical sensor of the present invention, when a user pulls out the liquid blocking film, the measured data with respect to the standard liquid is obtained. Then, a user sprays the liquid to be measured to the liquid retaining material or immerses the liquid retaining material into the liquid to be measured. Thereby, the measured data with respect to the liquid to be measured is obtained. Accordingly, a user can perform measurement with a simple operation. Particularly, when a liquid to be measured discharged from a living body (urine, for example) is directly sprayed to the liquid retaining material from the living body, it is unnecessary for a user to prepare a container for storing the liquid to be measured or instrument for handling the liquid to be measured and hence, the method becomes convenient.

Effects of the Invention

As can be clearly understood from above, according to the sensor head of the present invention, calibration for electrochemical measurement can be performed with a simple operation, and the sensor head can be miniaturized and can be manufactured at a low cost.

Further, in the electrochemical sensor of the present invention, calibration of the sensor head can be performed with simple operation, and the electrochemical sensor can be miniaturized as well as be manufactured at a low cost.

Still further, according to the method of using an electrochemical sensor of the present invention, measurement can be performed with simple operation.

BRIEF DESCRIPTION OF THE DRAWINGS

FIG. 17A and FIG. 17B are block diagrams respectively showing a constitution of a measurement system used in verification experiments carried out for respective sensor heads.

EMBODIMENTS OF THE INVENTION

Figure 1:
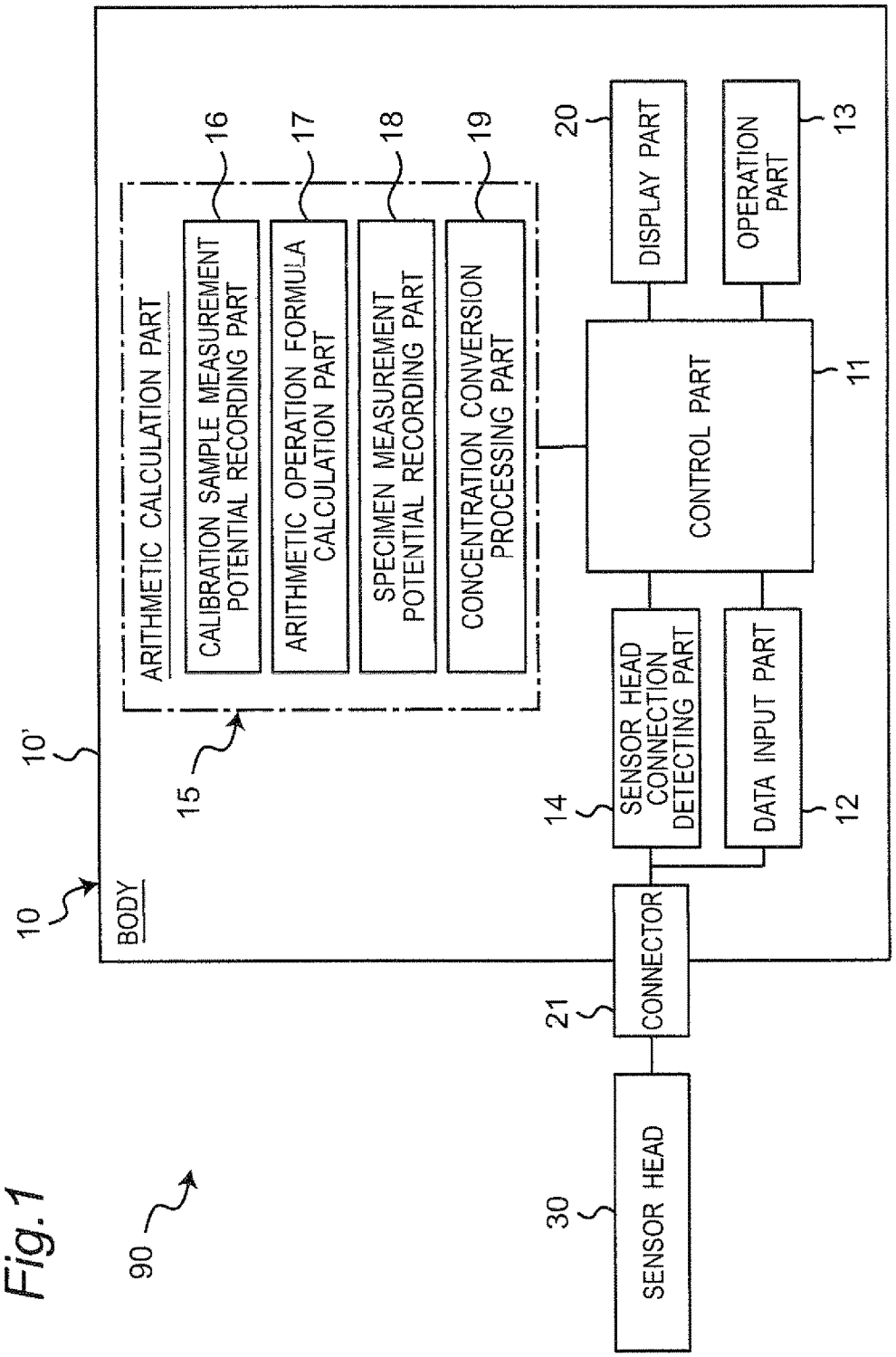
FIG. 1 is a block diagram showing a constitution of an electrochemical sensor according to one embodiment of the present invention.

The present invention is explained in detail in conjunction with embodiments shown in the drawings.

(First Embodiment)

FIG. 1 shows a block diagram showing a constitution of an electrochemical sensor (the whole sensor being indicated by symbol 90) according to one embodiment of the present invention.

The electrochemical sensor 90 substantially includes a sensor head 30 and a body 10 having a casing 10'. The body 10 includes a connector 21 to which the sensor head 30 is detachably mounted. The connector 21 is provided in a state where the connector 21 penetrates a wall surface of the casing 10'. In the body 10, a control part 11, a data input part 12, an operation part 13, a sensor head connection detection part 14, and a display part 20 are mounted and housed. The control part 11 includes an arithmetic calculation part 15 described later.

In this embodiment, the body 10 has an elongated angular columnar profile for allowing a user to hold the body 10 with his hand. The sensor head 30 has an approximately rectangular plate shape. As a result, the electrochemical sensor 90 is configured as a hand holding type device that a user uses while holding the body 10 with his hand, which is described in detail later.

Figure 2A:
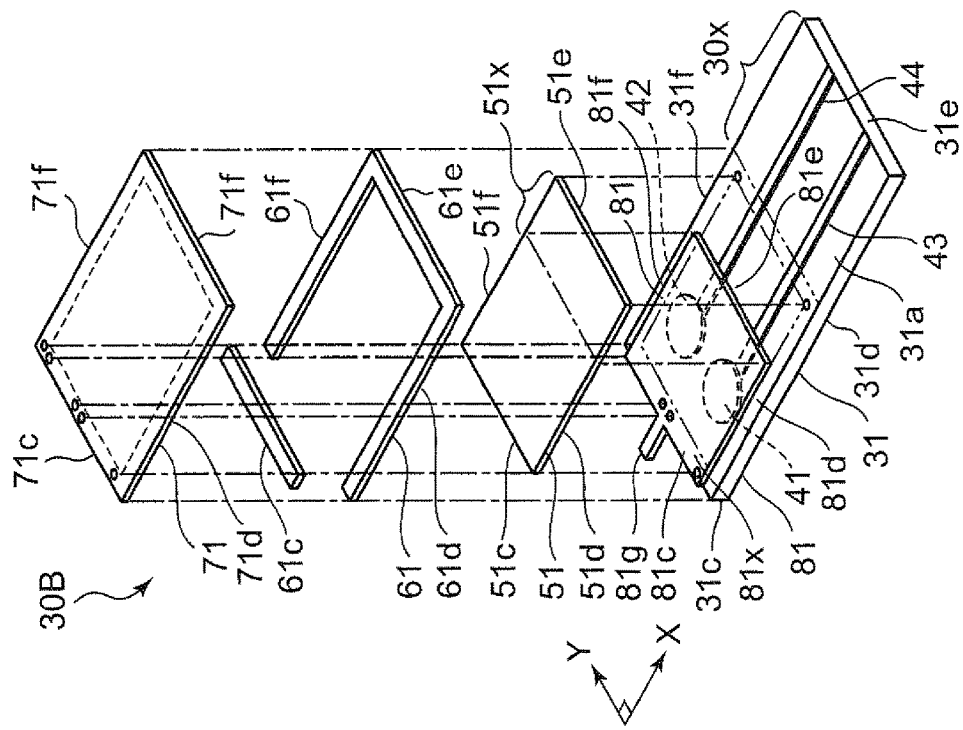
FIG. 2A is an exploded perspective view of a sensor head which is mountable on the electrochemical sensor shown in FIG. 1 where a liquid retaining material and electrodes are brought into direct contact with each other (hereinafter referred to as "contact type").
Figure 3:
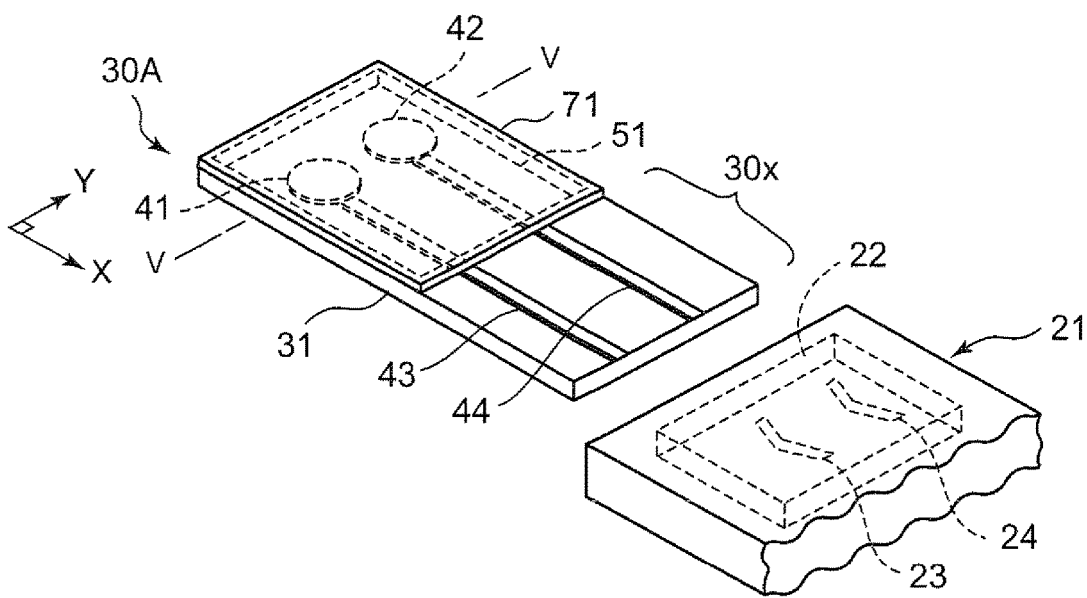
FIG. 3 is a perspective view showing the sensor head in a completed state corresponding to FIG. 2A together with a connector corresponding to the sensor head.

The sensor head 30 can take some configurations in accordance with the present invention. FIG. 2A shows in an exploded state a contact type sensor head 30A as one example of the sensor head 30. FIG. 3 shows a completed state of the sensor head 30A. "Contact type" means that a liquid retaining material 51 and electrodes 41, 42 described later are brought into direct contact with each other.

As can be clearly understood from FIG. 2A, the sensor head 30A includes: a rectangular substrate 31 having a predetermined size; a first electrode 41 and a second electrode 42 having a circular disc shape or a circular columnar shape and arranged on a mounting surface 31a which constitutes one of main surfaces of the substrate 31 in a spaced-apart manner along one side 31c; and a first pullout electrode 43 and a second pullout electrode 44 extending in parallel to each other in the X direction from the first and the second electrodes 41, 42 toward an opposite side (edge portion) 31e of the substrate 31.

The substrate 31 is made of an insulation material such as PET (polyethylene terephthalate), glass, silicon, a polyimide film or a glass epoxy. Accordingly, the mounting surface 31a also has insulation property. The first pullout electrode 43 and the second pullout electrode 44 are made of an electrically conductive material such as Pt, Ag, Au, Ir, C or $IrO_2$.

The sensor head 30A also includes a rectangular liquid retaining sheet 51 which constitutes a liquid retaining material on the mounting surface 31a thereof in such a manner that the liquid retaining sheet 51 integrally covers the first electrode 41 and the second electrode 42. The liquid retaining sheet 51 covers an approximately half of the mounting surface 31a close to a side 31c of the mounting surface 31a. A portion of the liquid retaining sheet 51 which faces the mounting surface 31a is adhered to the mounting surface 31a by an adhesive agent not shown (a double-sided adhesion tape may be used).

The liquid retaining sheet 51 is impregnated with a standard liquid which becomes a reference in electrochemical measurement. The liquid retaining sheet 51 has liquid permeation property which allows a liquid to be measured to permeate the liquid retaining sheet 51 therethrough toward the first electrode 41 and the second electrode 42. Accordingly, it is possible to easily bring the liquid retaining sheet 51 into a state where the standard liquid in the liquid retaining sheet 51 is replaced with the liquid to be measured by spraying the liquid to be measured to the liquid retaining sheet 51 or by immersing the liquid retaining sheet 51 in the liquid to be measured.

The liquid retaining sheet 51 is, in this embodiment, made of a paper-like material which is formed by aggregating fibers. Besides such a material, as the material for forming the liquid retaining sheet 51, various materials can be adopted including a gel-like material such as agar, gelatin, agarose gel, cellulose gel or polyacrylamide, a cloth-like material formed by aggregating fibers or a porous material such as sponge, for example. It is desirable that the liquid retaining sheet 51 has resistance to the standard liquid. Accordingly, the liquid retaining sheet 51 can maintain a state where the liquid retaining sheet 51 is impregnated with the standard liquid over a long period. This brings about an advantageous effect when the sensor head 30A is placed on a market as a commercially available product, for example.

The sensor head 30A also includes a rectangular sealing sheet 71 as a sealing member which covers the liquid retaining sheet 51 for preventing a change in the standard liquid impregnated into the liquid retaining sheet 51.

In this embodiment, the sealing sheet 71 has a planar direction size larger than a planar direction size of the liquid retaining sheet 51. On the mounting surface 31a, four sides 51c, 51d, 51e, 51f of the liquid retaining sheet 51 are arranged at positions retracted inwardly from four sides 71c, 71d, 71e, 71f of the sealing sheet 71 by a predetermined size. Three sides 71c, 71d, 71f of the sealing sheet 71 are arranged at positions where these sides 71c, 71d, 71f coincide with three sides 31c, 31d, 31f of the substrate 31. Edge portions of the sealing sheet 71 along four sides 71c, 71d, 71e, 71f (portions of the sealing sheet 71 positioned outside the liquid retaining sheet 51) are hermetically adhered to the mounting surface 31a by way of a double-sided adhesive tape 61 having rectangular frame shape. The sealing sheet 71 is configured in form of a sheet in the same manner as the liquid retaining sheet 51 and hence, the sensor head 30A can be formed with a small thickness.

With the use of the sealing sheet 71, it is possible to prevent a change in the standard liquid impregnated into the liquid retaining sheet 51. Accordingly, calibration with high degree of accuracy can be realized. This brings about an advantageous effect that, for example, when the sensor head 30A is placed on a market as a commercially available product, it is possible to ensure a long period during which the sensor head 30A can be calibrated with high degree of accuracy using the standard liquid. It is desirable that the sealing sheet 71 is removed by a user immediately before the sensor head 30A is used. The sealing sheet 71 is adhered to the mounting surface 31a by way of the double-sides adhesive tape 61 and hence, a user can easily remove the sealing sheet 71 using his nail.

As can be easily understood from FIG. 3, on a portion 30x of the sensor head 30A which is not covered with the sealing sheet 71 (the portion 30x hereinafter referred to as "electrode pad portion") 30x, the first pullout electrode 43 and the second pullout electrode 44 are exposed.

Figure 5:
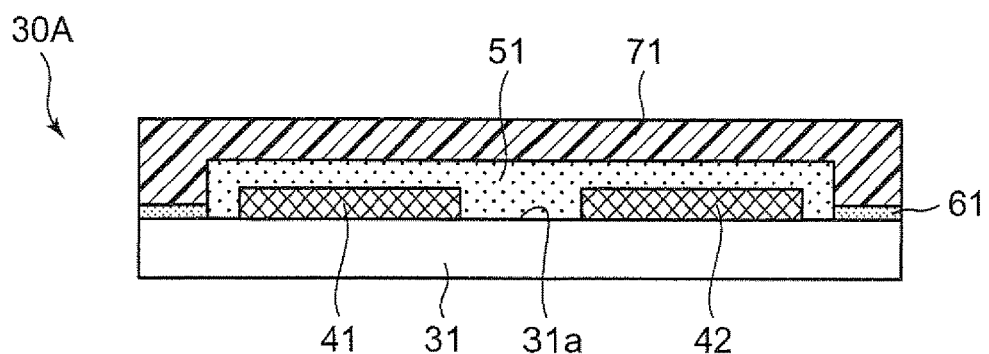
FIG. 5 is a view showing a cross section (corresponding to a cross section taken along a line V-V in FIG. 3) of the sensor head of the contact type in a completed state.

As shown in FIG. 5 (corresponding to a cross section taken along a line V-V in FIG. 3), in this embodiment (contact type), the liquid retaining sheet 51 is brought into direct contact with the first electrode 41 and the second electrode 42. Accordingly, at a point of time that a user intends to use the sensor head 30A, the sensor head 30A is already brought into a state where the standard liquid exudes from the liquid retaining sheet 51 and is brought into contact with the first electrode 41 and the second electrode 42.

The sensor head 30A having the above-mentioned constitution has the relatively small number of constitutional elements and hence, the sensor head 30A can be miniaturized and can be also manufactured at a low cost.

The connector 21 shown in FIG. 1 includes, as specifically shown in FIG. 3, a slot 22 into which the electrode pad portion 30x of the sensor head 30A is to be inserted. In the inside of the slot 22, contact members 23, 24 formed of an L-shaped leaf spring are provided at positions corresponding to the first pullout electrode 43 and the second pullout electrode 44 of the sensor head 30A. When a user inserts the electrode pad portion 30x of the sensor head 30A into the inside of the slot 22, the first pullout electrode 43 and the second pullout electrode 44 are brought into contact with the contact members 23, 24, thus becoming electrically conductive with the contact members 23, 24. As a result, a potential difference or an electric current between the first electrode 41 and the second electrode 42 of the sensor head 30A can be detected by the body 10 by way of the connector 21.

In a state where the sensor head 30A is mounted on the body 10 by way of the connector 21, a portion of the sensor head 30A where the liquid retaining sheet 51 is arranged is configured to project to the outside from the body 10. Thereby, a user can easily perform an operation of spraying a liquid to be measured to the liquid retaining sheet 51 or an operation of immersing the liquid retaining sheet 51 in the liquid to be measured by holding the body 10 with his hand.

The data input part 12 mounted on the body 10 shown in FIG. 1 inputs a potential difference or an electric current between the first electrode 41 and the second electrode 42 of the sensor head 30A.

The sensor head connection detection part 14 detects whether or not the sensor head 30A is mounted on the body 10 based on whether or not the contact members 23, 24 of the connector 21 are opened with each other. A limit switch (not shown in the drawing) may be provided in the inside of the slot 22 shown in FIG. 3. The sensor head connection detection part 14 may detect whether or not the sensor head 30A is mounted on the body 10 based on whether or not a portion of the substrate 31 is brought into contact with the limit switch so that the limit switch is turned on.

The control part 11 in FIG. 1 includes a CPU (Central Processing Unit) which is operated in accordance with software, and controls an operation of the whole electrochemical sensor 90. Particularly, the control part 11 includes an arithmetic operation part 15 which constitutes a detection part. The arithmetic operation part 15 includes: a calibration sample measurement potential recording part 16; an arithmetic operation formula calculation part 17; a specimen measurement potential recording part 18; and a concentration conversion processing part 19, which will be explained in detail later.

Figure 13:
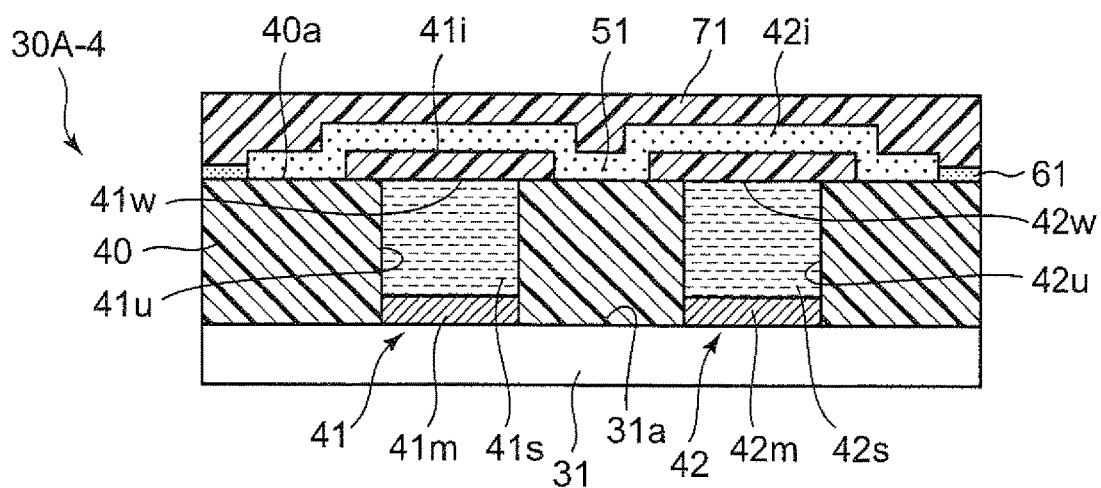
FIG. 13 is a cross-sectional view showing still another constitutional example of the contact type sensor head.
Figure 14:
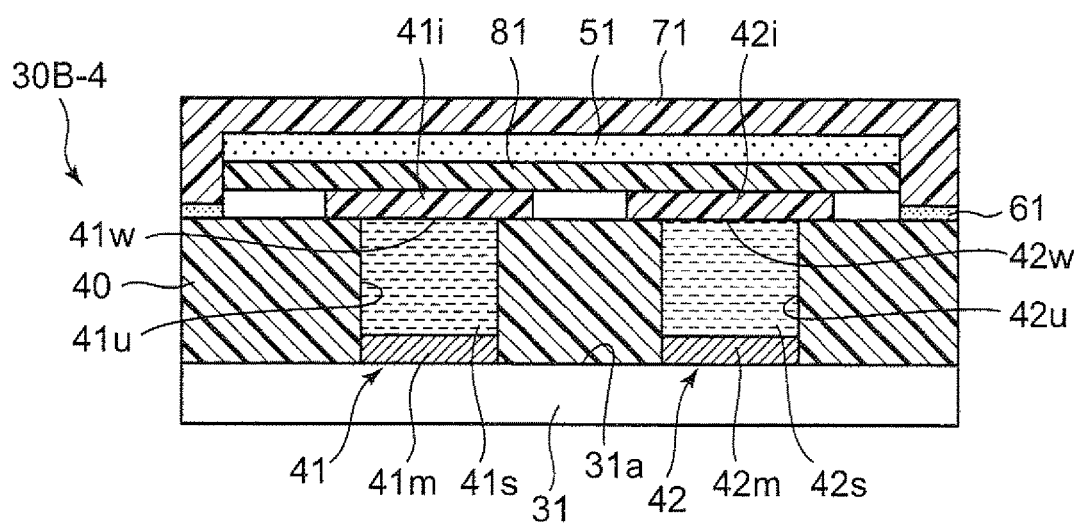
FIG. 14 is a cross-sectional view showing still another constitutional example of the pullout type sensor head.

The operation part 13 shown in FIG. 13 is formed of a push button switch in this embodiment, and allows a user to input an instruction for starting measurement of a liquid to be measured.

The display part 20 is constituted of an LCD (liquid crystal display element) in this embodiment. The display part 20 displays various information such as a result of an arithmetic operation by the control part 11.

Immediately before using the electrochemical sensor 90, a user removes the sealing sheet 71 from the sensor head 30A, and mounts the electrode pad portion 30x of the sensor head 30A in the connector 21 of the body 10. At this point of time, in the sensor head 30A, the standard liquid has already exuded from the liquid retaining sheet 51 and is brought into contact with the first electrode and the second electrode.

When the sensor head 30A is mounted on the body 10, the sensor head connection detection part 14 detects this mounting, and the arithmetic operation part 15 functions as a first control part in response to the detection, and detects a potential difference or an electric current between the first electrode 41 and the second electrode 42. Due to such an operation, measured data (a potential difference or an electric current, the same definition being applicable hereinafter) is readily obtained with respect to the standard liquid. The calibration sample measurement potential recording part 16 stores measured electrochemical data with respect to the standard liquid. Accordingly, a user can perform calibration without intentionally performing an operation for such calibration.

After measured data is obtained with respect to the standard liquid, the user brings the sensor head 30A into a state where the standard liquid in the liquid retaining sheet 51 is replaced with the liquid to be measured by spraying the liquid to be measured to the liquid retaining sheet 51 or by immersing the liquid retaining sheet 51 into the liquid to be measured. In such a state, the user inputs an instruction for starting measurement with respect to the liquid to be measured by operating the operation part 13 of the body 10 (by pushing down the push button switch in this embodiment). The arithmetic operation part 15 functions as a second control part in response to the instruction, and detects a potential difference or an electric current between the first electrode 41 and the second electrode 42. Due such an operation, measured data (a potential difference or an electric current, the same definition being applicable hereinafter) is obtained with respect to the liquid to be measured. The specimen measurement potential recording part 18 stores measured data with respect to the liquid to be measured.

Thereafter, the arithmetic operation part 15 functions as a third control part, that is, the arithmetic operation formula calculation part 17 calibrates the measured data with respect to the liquid to be measured using the measured data with respect to the standard liquid (concentration of the standard liquid known), and the concentration conversion processing part 19 outputs a signal indicative of measured electrochemical data (concentration of specific component in this embodiment) with respect to the liquid to be measured. Accordingly, the measured electrochemical data with respect to the liquid to be measured can be obtained with high degree of accuracy.

In this manner, according to the electrochemical sensor 90 of this embodiment, a user can perform measurement with a simple operation without intentionally performing an operation for calibration. Particularly, when the liquid to be measured (urine, for example) discharged from a living body is directly sprayed to the liquid retaining sheet 51 from the living body, it is unnecessary for a user to prepare a container for accommodating liquid to be measured or instrument for handling the liquid to be measured and hence, the electrochemical sensor 90 becomes convenient. Further, the electrochemical sensor 90 can be used in a place where a piping facility for measurement is not available.

Since the sensor head 30A can be miniaturized and manufactured at a low cost, the electrochemical sensor 90 can be also miniaturized as a whole and can be manufactured at a low cost.

After measured electrochemical data is obtained with respect to the liquid to be measured, the sensor head 30A can be easily removed from the connector 21. Thereby, the sensor head 30A also has an advantage that the sensor head 30A is easily disposable along with advantages that the sensor head 30A can be miniaturized and manufactured at a low cost. Accordingly, the sensor head 30A is suitable for obtaining data on a contaminated object to be measured or a contaminated environment (the sensor head 30A being disposable after the sensor head 30A is used).

In the constitution where the electrode pad portion 30x is exposed as in the case of the above-mentioned sensor head 30A, a user may remove the sealing sheet 71 immediately before the liquid to be measured is sprayed to the sensor head 30A or the sensor head 30A is immersed in the liquid to be measured, instead of removing the sealing sheet 71 before mounting the sensor head 30A on the sensor body 10.

(Second Embodiment)

In the above-mentioned embodiment, the sealing sheet 71 provided in a sheet form is used as the sealing member. However, the sealing member is not limited to the sealing sheet 71. A sealing pack 72 provided in a bag form may be used as a sealing member in place of the sealing sheet 71 as shown in FIG. 4.

Figure 4:
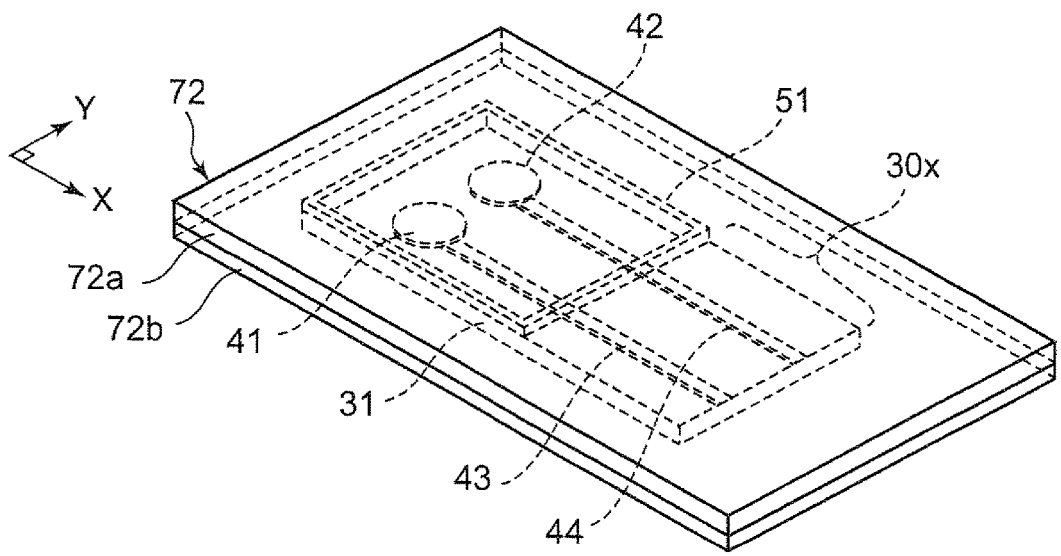
FIG. 4 is a view showing the sensor head in a completed state where the sensor head is covered with a sealing member in form of a bag.

In the embodiment shown in FIG. 4, the sealing pack 72 is constituted of a rectangular front sheet 72a and rear sheet 72b having a planar direction size larger than a planar direction size of a substrate 31. The front sheet 72a and the rear sheet 72b have at least four sides thereof hermetically adhered to each other, and cover a whole substrate 31 including the mounting surface 31a together with the first electrode 41, the second electrode 42 and a liquid retaining sheet 51. Even when a sensor head includes such a sealing pack 72, the reduction in thickness of the sensor head is not obstructed. Further, the sealing pack 72 can surely prevent the evaporation of the standard liquid impregnated into the liquid retaining sheet 51. The sealing pack 72 is expected to be removed before the sensor head is mounted on a sensor body 10.

The sensor head may be configured such that a size of the sealing pack 72 is approximately halved with respect to the direction that pullout electrodes 43, 44 extend (X direction) so that the sealing pack 72 covers only an approximately half portion of the substrate 31 (on a side where the liquid retaining sheet 51 is arranged) and an electrode pad portion 30x is exposed. In such a constitution, a user may remove the sealing pack 72 not before mounting the sensor head on the sensor body 10 but immediately before the liquid to be measured is sprayed to the sensor head or the sensor head is immersed into the liquid to be measured.

(Third Embodiment)

Figure 7:
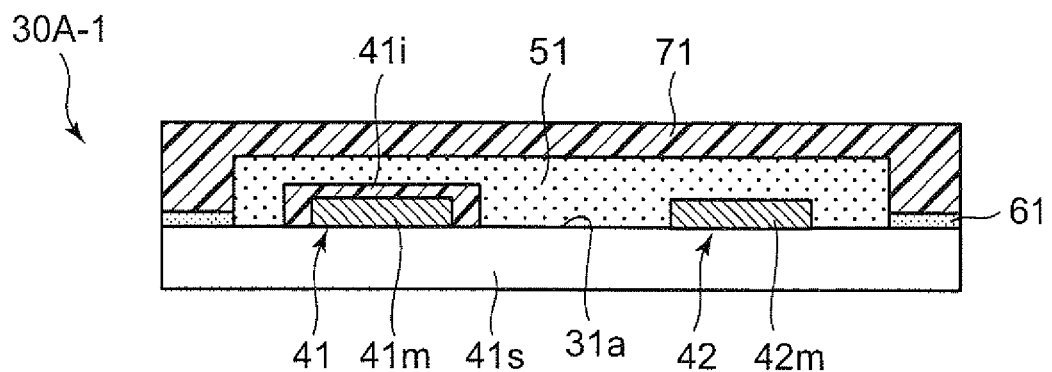
FIG. 7 is a cross-sectional view showing one constitutional example of the contact type sensor head.
Figure 8:
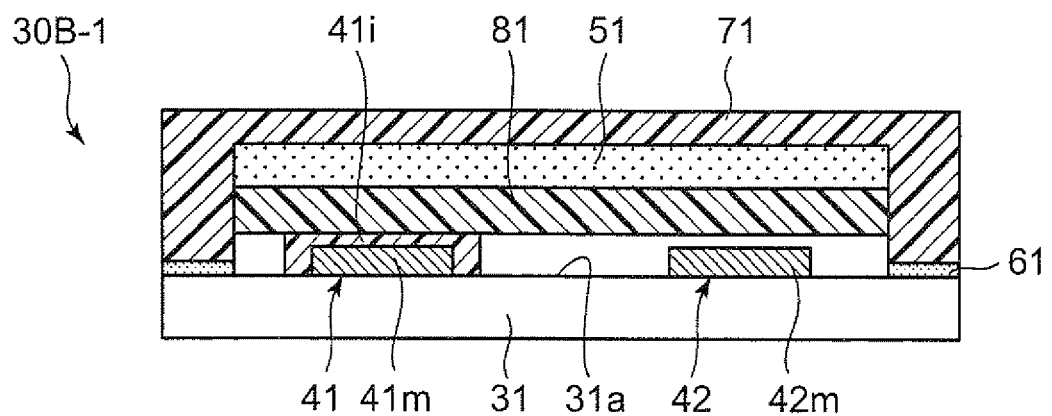
FIG. 8 is a cross-sectional view showing one constitutional example of the pullout type sensor head.

FIG. 7 shows one specific constitutional example (indicated by a symbol 30A-1) where the sensor head 30A shown in FIG. 3 can be adopted as an ion sensor.

In the sensor head 30A-1 according to this embodiment, the first electrode 41 is constituted of a first core material $41m$ having electric conductivity, and an ion selection film $41i$ which is formed in contact with a surface of the first core material $41m$ and selectively allows permeation of a specific ion species contained in the liquid to be measured therethrough or absorption of the specific ion species therein. The first electrode 41 constitutes an ion selection electrode. On the other hand, the second electrode 42 is constituted of only an electrically conductive material (second core material) $42m$ and constitutes a reference electrode which is a non-sensitive electrode.

The concentration of a specific ion species (hereinafter also referred to as "specific ion" when appropriate) contained in the liquid to be measured is obtained based on the following principle using the sensor head 30A-1 shown in FIG. 7.

In general, a potentiometric sensor which measures the ion concentration based on an electrode potential exhibits a response proportional to a logarithm (log) of activity of a chemical species in accordance with a Nernst equation expressed by the following formula (1).

$$E = E^* + S \log a \tag{1}$$

Here, F is a potential of an ion selection electrode, $E^*$ is an intrinsic formal potential at each electrode, S is a Nernst constant expressing a theoretical potential gradient of the ion selection electrode, and "a" indicates ion activity at a boundary of the electrode. Activity means a rate of the number of particles of a material which occupies in a mixed product. In a typical dilute solution which constitutes the liquid to be measured, the ion activity can be replaced with a volumetric molar concentration C.

Taking into account the ion selection electrode 41 and the reference electrode 42 which always exhibits a fixed potential, and assuming a reference potential in the system as $E_0$, a potential difference $E_w$ between the ion selection electrode 41 and the reference electrode 42 is expressed by the formula (2) in general.

$$E_w = E_0 + S \log C \tag{2}$$

To obtain the concentration of specific ion contained in the liquid to be measured, it is necessary to obtain in advance a potential gradient (Nernst constant) S and a reference potential $E_0$ in the system. These values S, $E_0$ are obtained by calibration. Here, with respect to the potential gradient S, a known fixed value which is measured in advance is adopted on the assumption that the potential gradient S is fixed within lots of manufactured sensors. The reference potential $E_0$ can be obtained by detecting a potential difference between the ion selection electrode 41 and the reference electrode 42 with respect to the standard liquid impregnated into a liquid retaining sheet 51. That is, assuming the concentration (known value) of specific ion in the standard liquid as $C_{ref}$ and the potential difference detected with respect to the standard liquid as $E_{ref}$, the following formula (3) is obtained from the formula (2).

$$E_0 = E_{ref} - S \log C_{ref} \tag{3}$$

A potential difference between the ion selection electrode 41 and the reference electrode 42 is detected with respect to the liquid to be measured in a state where the standard liquid in the liquid retaining sheet 51 is replaced with the liquid to be measured by spraying the liquid to be measured to the liquid retaining sheet 51 or by immersing the liquid retaining sheet 51 into the liquid to be measured. Assuming the concentration of a specific ion in the liquid to be measured as $C_s$ and a potential difference detected with respect to the liquid to be measured as $E_s$, the following formula is obtained.

$$\log C_s = (E_s - E_0)/S$$

Accordingly, the concentration $C_s$ of the specific ion in the liquid to be measured is obtained by the following formula (4).

$$C_s = 10^{\{(E_s - E_0)/S\}} = 10^{\{(E_s - E_{ref} + S \log C_{ref})/S\}} \tag{4}$$

Figure 15:
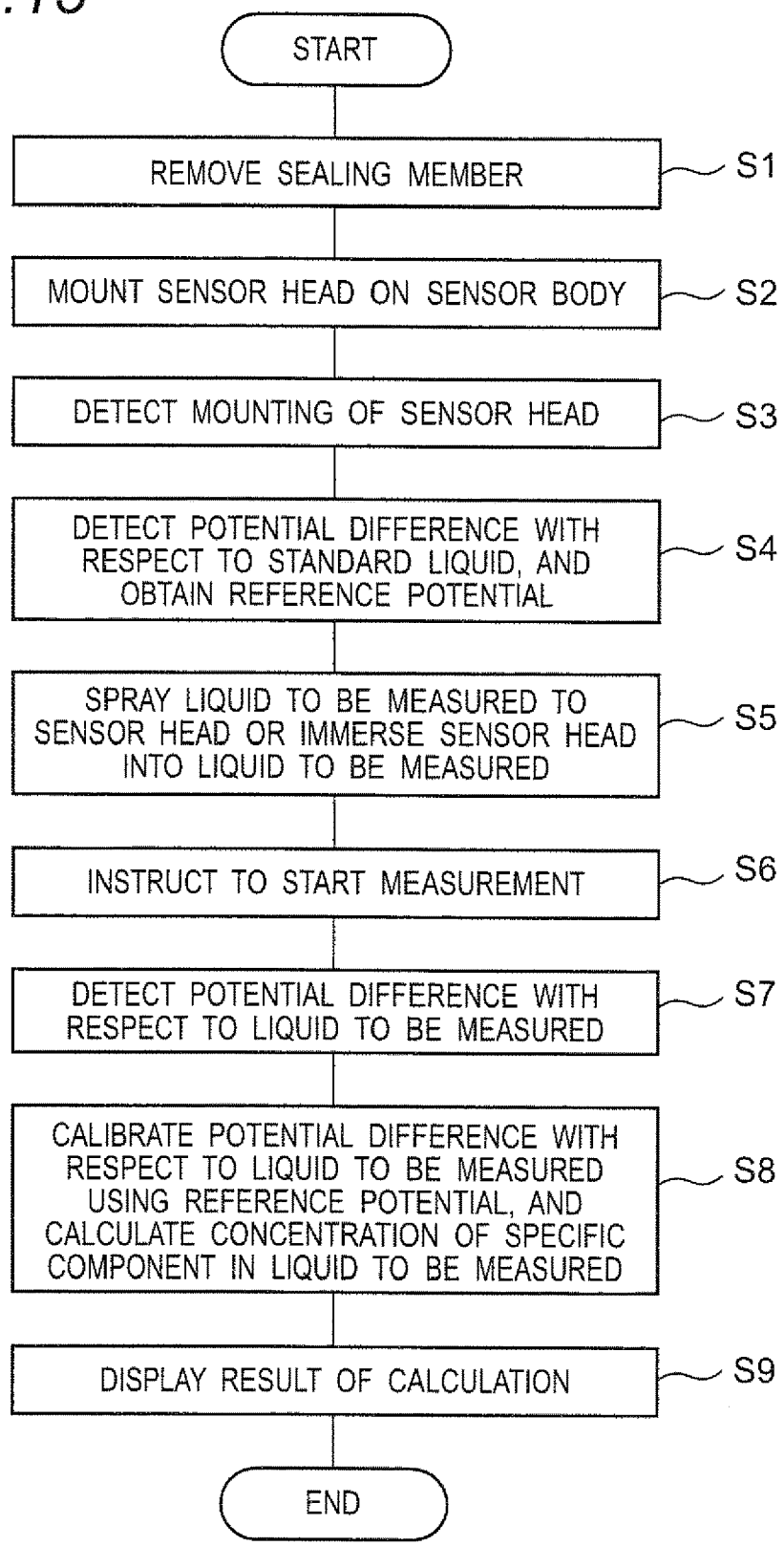
FIG. 15 is a flowchart showing an operation flow when the concentration of a specific component in a liquid to be measured is measured using the electrochemical sensor having the contact type sensor head.

FIG. 15 shows a flow of a method of using the electrochemical sensor 90 when a user uses the electrochemical sensor 90 with the sensor head 30A-1 shown in FIG. 7.

Firstly, as indicated in step S1 shown in FIG. 15, a user removes a sealing sheet 71 which constitutes a sealing member from the sensor head 30A-1. As described previously, at a point of time that the user intends to use the sensor head 30A-1, the standard liquid has already exuded from the liquid retaining sheet 51 so that the sensor head 30A-1 is brought into a state where the standard liquid is in contact with the first electrode 41 and the second electrode 42.

Next, as indicated in step S2 shown in FIG. 15, the user mounts the sensor head 30A-1 on the sensor body 10. Specifically, the user mounts the electrode pad portion 30x (see FIG. 3) of the sensor head 30A-1 on the connector 21.

In response to such mounting of the sensor head 30A-1, as indicated in step S3 shown in FIG. 15, the sensor head connection detection part 14 in the body 10 detects that the sensor head 30A-1 is mounted on the body 10.

Then, the control part 11 functions as a first control part and starts a first control. In this control, as indicated in step S4 shown in FIG. 15, the control part 11 operates the arithmetic operation part 15 as a detection part so that the arithmetic operation part 15 detects a potential difference $E_{ref}$ with respect to the standard liquid. Specifically, the data input part 12 inputs the potential difference $E_{ref}$ between the first electrode 41 and the second electrode 42 of the sensor head 30A-1 by way of the connector 21 shown in FIG. 1, and the calibration sample measurement potential recording part 16 stores the potential difference $E_{ref}$. The arithmetic operation formula calculation part 17 performs an arithmetic operation for calculating a reference potential $E_0$ based on the formula (3) using the potential difference $E_{ref}$ with respect to the standard liquid in order to calibrate the potential difference $E_s$ with respect to the liquid to be measured. Accordingly, the user can perform calibration without intentionally performing operations for calibration.

When the arithmetic operation by the arithmetic operation formula calculation part 17 is completed, the control part 11 displays on the display part 20 that measurement preparation with respect to the liquid to be measured is completed (a row characters which says "measurement preparation completed", for example), thus informing a user of the completion.

Next, as indicated in step S5 shown in FIG. 15, the user sprays the liquid to be measured to the sensor head 30A-1 or immerses the sensor head 30A-1 into the liquid to be measured. By continuing the spraying of the liquid to be measured to the sensor head 30A-1 or the immersion of the sensor head 30A-1 in the liquid to be measured for 20 to 30 seconds, the sensor head 30A-1 is brought into a state where the standard liquid in the liquid retaining sheet 51 is replaced with the liquid to be measured. Accordingly, the sensor head 30A-1 is brought into a state where the liquid to be measured permeates the liquid retaining sheet 51 and is brought into contact with the first electrode 41 and the second electrode 42.

In this state, as indicated in step S6 shown in FIG. 15, the user operates the operation part 13 of the body 10 so as to input an instruction for starting measurement with respect to the liquid to be measured.

Then, the control part 11 functions as a second control part and starts a second control. In this control, as indicated in step S7 shown in FIG. 15, the control part operates the arithmetic operation part 15 which constitutes a detection part so that the arithmetic operation part 15 detects a potential difference $E_s$ with respect to the liquid to be measured. Specifically, the data input part 12 inputs the potential difference $E_s$ between the first electrode 41 and the second electrode 42 of the sensor head 30A-1 by way of the connector 21 shown in FIG. 1, and a specimen measurement potential recording part 18 stores the potential difference $E_s$.

Subsequently, the control part 11 functions as a third control part and starts a third control. As indicated in step S8 shown in FIG. 15, the control part 11 calibrates the potential difference with respect to the liquid to be measured using the potential difference with respect to the standard liquid, and calculates a concentration of a specific component in the liquid to be measured. Specifically, the concentration conversion processing part 19 calculates the concentration $C_s$ of the specific ion in the liquid to be measured based on the formula (4).

As the last step, as indicated in step S9 shown in FIG. 15, the control part 11 displays, on the display part 20, an information indicative of the concentration $C_s$ of the specific ion in the liquid to be measured as a result of the arithmetic, operation.

In this manner, the user can perform measurement by simple operations.

(Fourth Embodiment)

Figure 9:
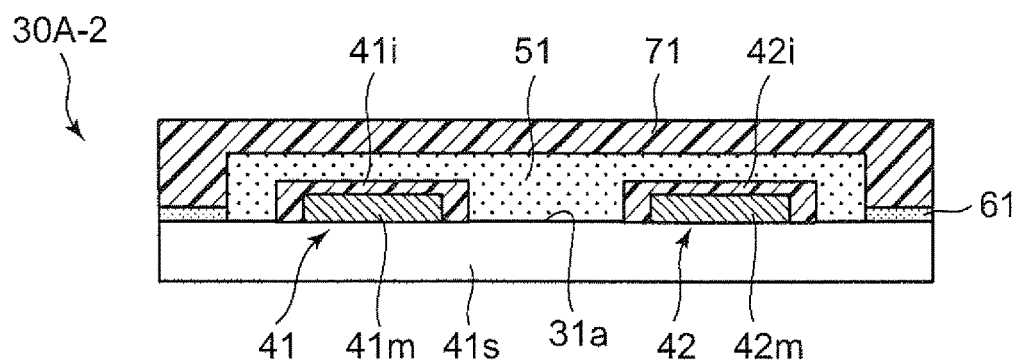
FIG. 9 is a cross-sectional view showing another constitutional example of the contact type sensor head.
Figure 10:
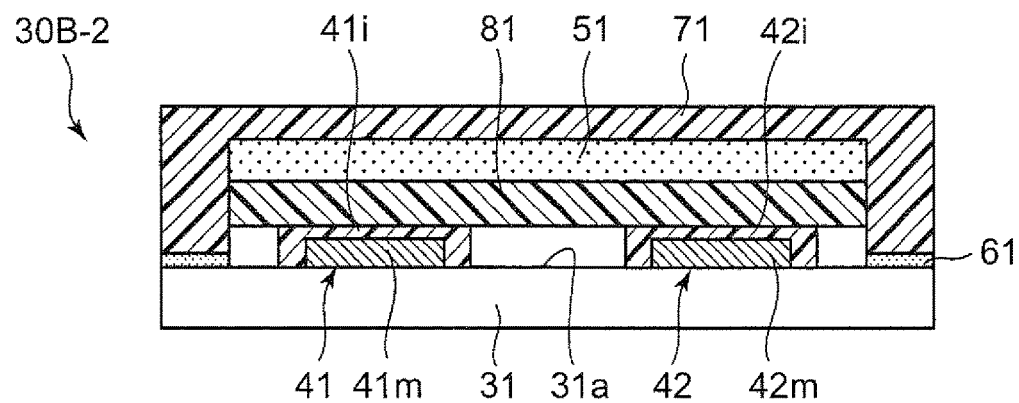
FIG. 10 is a cross-sectional view showing another constitutional example of the pullout type sensor head.

FIG. 9 shows another constitutional example (indicated by a symbol 30A-2) where the sensor head 30A shown in FIG. 3 can be adopted as an ion sensor.

In the sensor head 30A-2 according to this embodiment, the first electrode 41 is constituted of a first core material 41m having electric conductivity, and a first ion selection film 41i which is formed in contact with a surface of the first core material 41m. The first electrode 41 constitutes an ion selection electrode (hereinafter referred to as "ion selection electrode 41" when appropriate). In the same manner, the second electrode 42 is constituted of a second core material 42 having electric conductivity, and a second ion selection film 42i which is formed in contact with a surface of the second core material 42. The second electrode 42 constitutes an ion selection electrode (hereinafter referred to as "ion selection electrode 42" when appropriate). The first ion selection film 41i and the second ion selection film 42i respectively have a property of selectively allowing permeation of ion species different from each other and contained in the liquid to be measured (these ion species being referred to as "first ion" and "second ion" when appropriated) therethrough or absorption of the specific ion species therein.

A concentration ratio between the first ion and the second ion contained in the liquid to be measured is obtained based on the following principle using the sensor head 30A-2 shown in FIG. 9.

Assume that the ion selection electrode 41 responds to the first ion with a potential gradient $S_1$, and the ion selection electrode 42 responds to the second ion with a potential gradient $S_2$. Here, assume the concentration of the first ion as $C_1$, and the concentration of the second ion as $C_2$ in a solution (including the standard liquid or the liquid to be measured). Assuming a reference potential in the system as $E_{0\_b}$, a potential difference $E_{w\_b}$ between the ion selection electrodes 41, 42 is expressed by the following formula (5).

$$E_{w\_b}=E_{0\_b}+S_1 \log C_1-S_2 \log C_2 \quad (5)$$

When the ion selection electrodes 41, 42 exhibit potential gradients (Nernst constants) which are substantially equal ($S_1=S_2$) with respect to the first ion and the second ion respectively, $E_{w\_b}$ is expressed by the following formula (6).

$$E_{w\_b}=E_{0\_b}+S_1 \log(C_1/C_2) \quad (6)$$

To obtain a concentration ratio between the first ion and the second ion contained in the liquid to be measured, it is necessary to obtain in advance a potential gradient (Nernst constant) $S_1$ and a reference potential $E_{0\_b}$ in the system. These values $S_1$ and $E_{0\_b}$ are obtained by calibration. Here, in the same manner as the third embodiment, with respect to the potential gradient $S_1$, a known fixed value which is measured in advance is adopted on the assumption that the potential gradient $S_1$ is fixed within lots of manufactured sensors. The reference potential $E_{0\_b}$ can be obtained by detecting a potential difference between the ion selection electrode 41 and the reference electrode 42 with respect to the standard liquid impregnated into a liquid retaining sheet 51. That is, assuming a concentration ratio (known value) between the first ion and the second ion with respect to the standard liquid as $M_{ref\_b}$ and a potential difference detected with respect to the standard liquid as $E_{ref\_b}$, the following formula (7) is obtained from the formula (6).

$$E_{0\_b}=E_{ref\_b}+S_1 \log(M_{ref\_b}) \quad (7)$$

A potential difference between the ion selection electrodes 41, 42 is detected with respect to the liquid to be measured in a state where the standard liquid in the liquid retaining sheet 51 is replaced with the liquid to be measured by spraying the liquid to be measured to the liquid retaining sheet 51 or by immersing the liquid retaining sheet 51 into the liquid to be measured. Assuming a concentration ratio between the first ion and the second ion in the liquid to be measured as $M_{s\_b}$ and a potential difference detected with respect to the liquid to be measured as $E_{s\_b}$, the following formula is obtained.

$$\log M_{s\_b}=(E_{s\_b}-E_{0\_b})/S_1$$

Accordingly, the concentration ratio $M_{s\_b}$ between the first ion and the second ion in the liquid to be measured is obtained by the following formula (8).

$$M_{s\_b}=10^{\{Es\_b-E0\_b)/S1\}}=10^{\{(Es\_b-Eref\_b+S1 \log Mref\_b)/S1\}} \quad (8)$$

Figure 16:
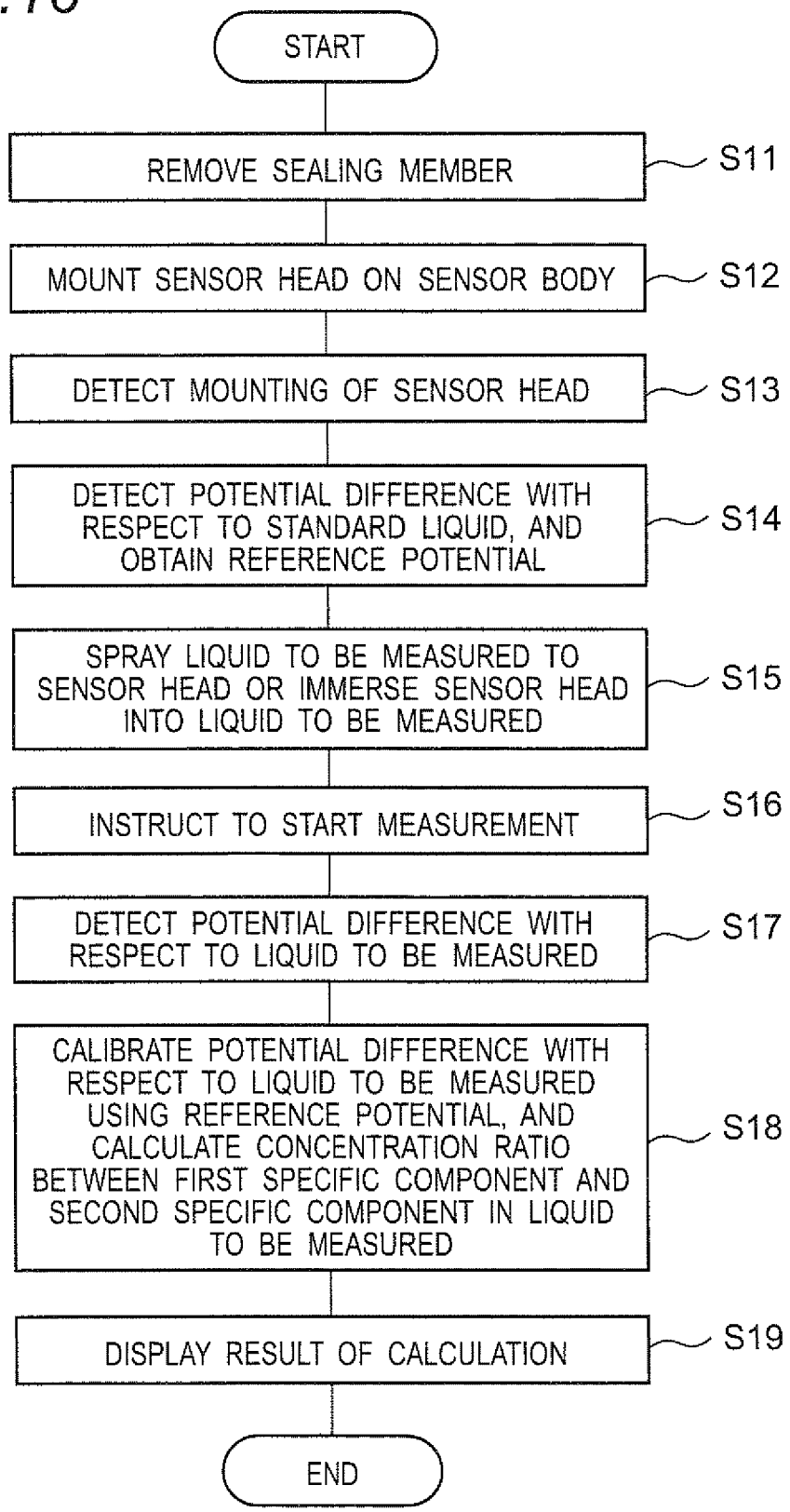
FIG. 16 is a flowchart showing an operation flow when a concentration ratio between a first specific component and a second specific component in a liquid to be measured is measured using the electrochemical sensor having the contact type sensor head.

FIG. 16 shows a flow of a method of using the electrochemical sensor 90 when a user uses the electrochemical sensor 90 with the sensor head 30A-2 shown in FIG. 9.

Firstly, as indicated in step S11 shown in FIG. 16, a user removes a sealing sheet 71 which constitutes a sealing member from the sensor head 30A-2. As described previously, at a point of time that the user intends to use the sensor head 30A-2, the standard liquid has already exuded from the liquid retaining sheet 51 so that the sensor head 30A-2 is brought into a state where the standard liquid is in contact with the first electrode 41 and the second electrode 42.

Next, as indicated in step S12 shown in FIG. 16, the user mounts the sensor head 30A-2 on the sensor body 10. Specifically, the user mounts the electrode pad portion 30x (see FIG. 3) of the sensor head 30A-2 in the connector 21.

In response to such mounting of the sensor head 30A-2, as indicated in step S13 shown in FIG. 16, the sensor head connection detection part 14 in the body 10 detects that the sensor head 30A-2 is mounted on the body 10.

Then, the control part 11 functions as a first control part and starts a first control. As indicated in step S14 shown in FIG. 16, the control part 11 operates the arithmetic operation part 15 which constitutes a detection part so that the arithmetic operation part 15 detects a potential difference $E_{ref\_b}$ with respect to the standard liquid. Specifically, the data input part 12 inputs the potential difference $E_{ref\_b}$ between the first electrode 41 and the second electrode 42 of the sensor head 30A-2 by way of the connector 21 shown in FIG. 1, and the calibration sample measurement potential recording part 16 stores the potential difference $E_{ref\_b}$. The arithmetic operation formula calculation part 17 performs an arithmetic operation for calculating a reference potential $E_{0\_b}$ based on the formula (7) using the potential difference $E_{ref\_b}$ with respect to the standard liquid in order to calibrate the potential difference $E_s$ with respect to the liquid to be measured. Accordingly, the user can perform calibration without intentionally performing operations for calibration.

When the arithmetic operation by the arithmetic operation formula calculation part 17 is completed, the control part 11 displays on the display part 20 that measurement preparation with respect to the liquid to be measured is completed (a row of characters which says "measurement preparation completed", for example), thus informing a user of the completion.

Next, as indicated in step S15 shown in FIG. 16, the user sprays the liquid to be measured to the sensor head 30A-2 or immerses the sensor head 30A-2 into the liquid to be measured. By continuing the spraying of the liquid to be measured to the sensor head 30A-2 or the immersion of the sensor head 30A-2 in the liquid to be measured for 20 to 30 seconds, the sensor head 30A-2 is brought into a state where the standard liquid in the liquid retaining sheet 51 is replaced with the liquid to be measured. Accordingly, the sensor head 30A-2 is brought into a state where the liquid to be measured permeates the liquid retaining sheet 51 and is brought into contact with the first electrode 41 and the second electrode 42.

In this state, as indicated in step S16 shown in FIG. 16, the user operates the operation part 13 of the body 10 so as to input an instruction for starting measurement with respect to the liquid to be measured.

Then, the control part 11 functions as a second control part and starts a second control. In this control, as indicated in step S17 shown in FIG. 16, the control part operates the arithmetic operation part 15 which constitutes a detection part so that the arithmetic operation part 15 detects a potential difference $E_{s\_b}$ with respect to the liquid to be measured. Specifically, the data input part 12 inputs the potential difference $E_{s\_b}$ between the first electrode 41 and the second electrode 42 of the sensor head 30A-2 by way of the connector 21 shown in FIG. 1, and the specimen measurement potential recording part 18 stores the potential difference $E_{s\_b}$.

Subsequently, the control part 11 functions as a third control part and starts a third control. In this control, as indicated in step S18 shown in FIG. 16, the control part 11 calibrates the potential difference with respect to the liquid to be measured using the potential difference with respect to the standard liquid, and calculates a concentration ratio between the first ion and the second ion in the liquid to be measured. Specifically, the concentration conversion processing part 19 calculates the concentration ratio $M_{s\_b}$ between the first ion and the second ion in the liquid to be measured based on the formula (8).

As the last step, as indicated in step S19 shown in FIG. 16, the control part 11 displays, on the display part 20, an information indicative of the concentration ratio $M_{s\_b}$ between the first ion and the second ion in the liquid to be measured as a result of the arithmetic operation.

In this manner, the user can perform measurement by simple operations.

(Fifth Embodiment)

Figure 11:
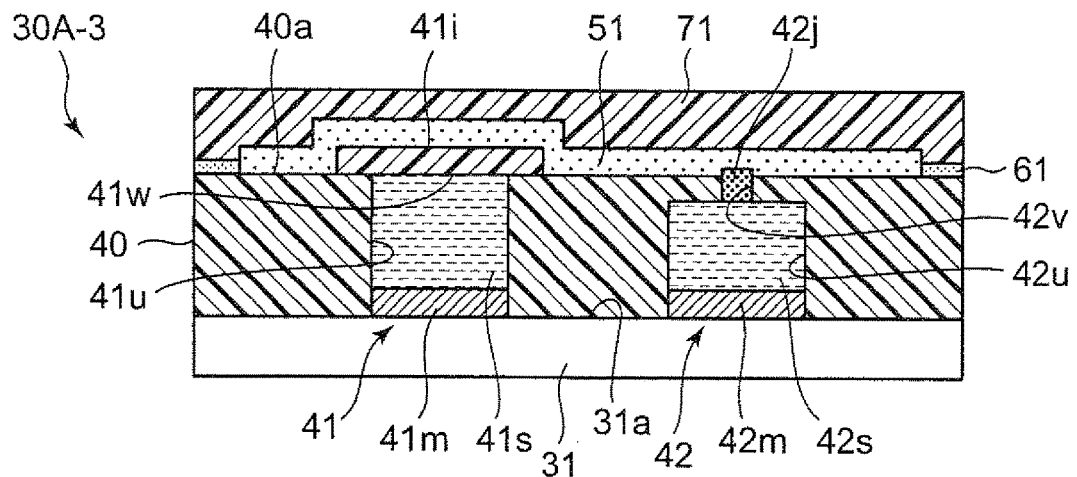
FIG. 11 is a cross-sectional view showing still another constitutional example of the contact type sensor head.
Figure 12:
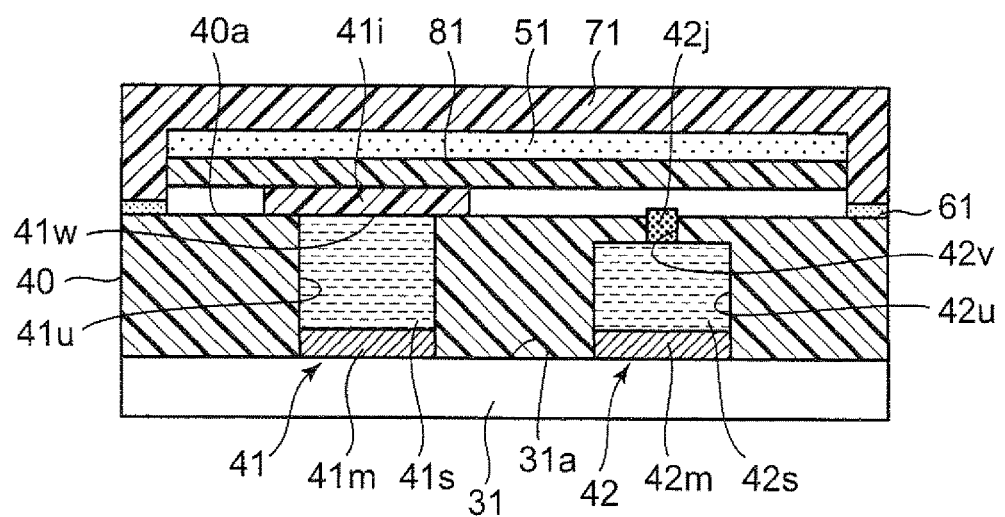
FIG. 12 is a cross-sectional view showing still another constitutional example of the pullout type sensor head.

FIG. 11 shows still another constitutional example (indicated by a symbol 30A-3) where the sensor head 30A shown in FIG. 3 can be adopted as an ion sensor.

In the sensor head 30A-3 according to this embodiment, the first electrode 41 includes a first core material 41m having electric conductivity, a first envelope 41u surrounding the first core material 41m and having insulation property, and a first inner liquid 41s for measurement of ion concentration which is filled between the first envelope 41u and the first core material 41m. The second electrode 42 includes a second core material 42m having electric conductivity, a second envelope 42u surrounding the second core material 42m and having insulation property, and a second inner liquid 42s for measurement of ion concentration which is filled between the second envelope 42u and the second core material 42m.

The first core material 41m and the second core material 42m have a circular shape substantially equal to the shapes of the first electrode 41 and the second electrode 42 shown in FIG. 2A with respect to a planar direction.

In the sensor head 30A-3 shown in FIG. 11, the first envelope 41u and the second envelope 42u are formed by providing circular holes in the rectangular plate-shaped insulation base material 40 having a planar direction size substantially equal to the planar direction size of the sealing sheet 71, the circular holes having planar direction sizes substantially equal to the planar direction sizes of the first core material 41m and the second core material 42m. The insulation base material 40 per se is hermetically laminated to the mounting surface 31a by an adhesive agent not shown in the drawing.

A first window portion 41w is formed in a portion of an upper surface 40a of the insulation base material 40 corresponding to the first envelope 41u in a state where the circular hole defining the first envelope 41u directly penetrates the portion in the plate thickness direction. On the other hand, a second window portion 42v is formed in a portion of the upper surface 40a of the insulation base material 40 corresponding to the second envelope 42u in a state where a circular hole which has a smaller diameter than the circular hole defining the second envelope 42u directly penetrates the portion in the plate thickness direction.

The ion selection film 41i which selectively allows a specific ion species contained in the liquid to be measured to permeate therethrough or to be absorbed therein is mounted on the first window portion 41w. On the other hand, a liquid path 42j which allows the communication between the standard liquid or the liquid to be measured and the second inner liquid 42s is formed in the second window portion 42v. As a material for farming the liquid path 42j, ceramic, agar or the like is used.

The liquid retaining sheet 51 same as the liquid retaining sheet 51 shown in FIG. 2A is mounted on the upper surface 40a of the insulation base material 40, and the sealing sheet 71 is mounted on the liquid retaining sheet 51 by way of the double-sided adhesive tape 61.

As a result, in the sensor head 30A-3 shown in FIG. 11, the first electrode 41 constitutes the ion selection electrode, and the second electrode 42 constitutes the reference electrode which is a non-sensitive electrode. As a material for forming the reference electrode which is a non-sensitive electrode, a silver/silver-chloride electrode, a silver/silver-iodide electrode, a calomel electrode or the like is used.

With the use of the sensor head 30A-3 shown in FIG. 11, the concentration of a specific ion species contained in the liquid to be measured can be obtained by the same principle and method explained in conjunction with the third embodiment.

Further, by selectively setting various materials for preparing a first inner liquid 41s and a second inner liquid 42s, it is possible to provide sensor heads for electrochemical measurement which can measure various ion species.

It is desirable that both a first inner liquid 41s and a second inner liquid 42s are equal to the standard liquid impregnated into the liquid retaining sheet 51 in composition. In this case, even when the first inner liquid 41s or the second inner liquid 42s is mixed with the standard liquid through the first window portion 41w or the second window portion 42v, no change occurs in the composition of the first inner liquid 41s, the second inner liquid 42s and the standard liquid. Accordingly, calibration can be performed with high degree of accuracy. This brings about an advantageous effect that, for example, when the sensor head 30A-3 shown in FIG. 11 is placed on a market as a commercially available product, it is possible to ensure a long period during which the sensor head 30A-3 can be calibrated with high degree of accuracy using the standard liquid.

It is desirable that the insulation base material 40 has resistance to a first inner liquid 41s, a second inner liquid 42s and the standard liquid. Accordingly, a state where the first envelope 41u and the second envelope 42u can preserve the first inner liquid 41s and the second inner liquid 42s can be maintained over a long period. This brings about an advantageous effect when the sensor head 30A-3 shown in FIG. 11 is placed on a market as a commercially available product, for example.

(Sixth Embodiment)

FIG. 13 shows still another constitutional example (indicated by a symbol 30A-4) where the sensor head 30A shown in FIG. 3 can be adopted as an ion sensor.

The sensor head 30A-4 according to this embodiment differs from the sensor head 30A-3 according to the embodiment shown in FIG. 11 with respect to a constitution of the second electrode 42. Other constitutional elements are constituted in the same manner as the sensor head 30A-3 according to the embodiment shown in FIG. 11.

In the sensor head 30A-4 shown in FIG. 13, in the same manner as the first window portion 41w in a portion of the upper surface 40a of the insulation base material 40 corresponding to the first envelope 41u, a second window portion 42w is formed in a portion of the upper surface 40a of the insulation base material 40 corresponding to the second envelope 42u in a state where a circular hole defining the second envelope 42u directly penetrates the portion in the plate thickness direction.

The first window portion 41w and the second window portion 42w are respectively provided with the first ion selection film 41i and the second ion selection film 42i which have a property of selectively allowing permeation of ions different from each other and contained in the liquid to be measured (these ion being referred to as "first ion" and "second ion" when appropriate) therethrough or absorption of the ions therein.

As a result, in the sensor head 30A-4 shown in FIG. 13, both the first electrode 41 and the second electrode 42 constitute an ion selection electrode, respectively.

With the use of the sensor head 30A-4, concentration ratio between the first ion and the second ion contained in the liquid to be measured can be obtained by the same principle and method explained in conjunction with the fourth embodiment.

Further, by selectively setting various materials for preparing the first inner liquid 41s and the second inner liquid 42s, it is possible to provide sensor heads for electrochemical measurement which can measure various ion species.

In the same manner as the case explained in conjunction with the fifth embodiment, it is desirable that both the first inner liquid 41s and the second inner liquid 42s are the same as the standard liquid impregnated into the liquid retaining sheet 51 in composition. Further, it is desirable that the insulation base material 40 has resistance to the first inner liquid 41s, the second inner liquid 42s and the standard liquid.

(Seventh Embodiment)

Figure 2B:
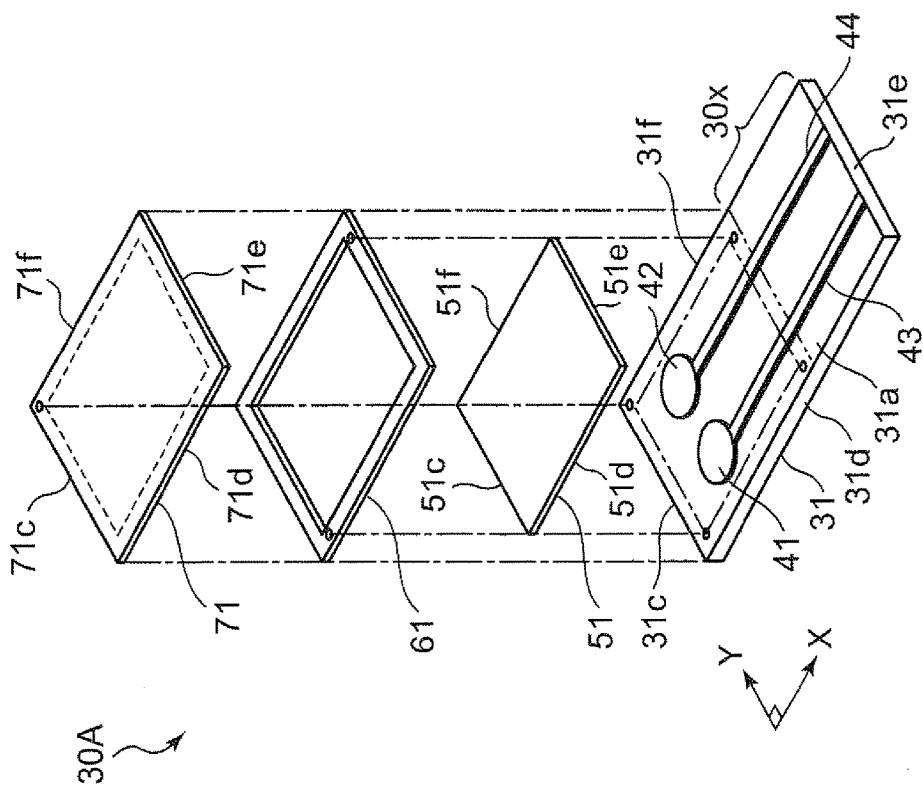
FIG. 2B is an exploded perspective view of a sensor head which is mountable on the electrochemical sensor shown in FIG. 1 where a liquid blocking film which is to be pulled out when used is present between a liquid retaining material and electrodes (hereinafter referred to as "pullout type").
Figure 6:
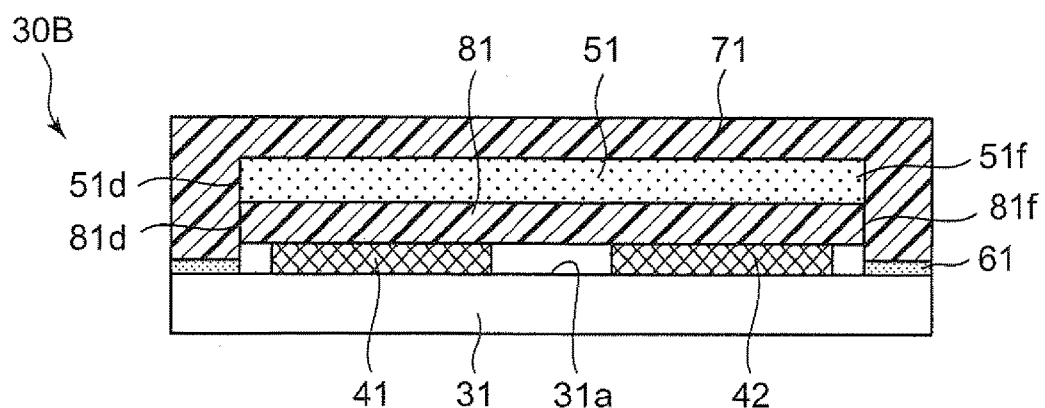
FIG. 6 is a view showing a cross section of the pullout type sensor head in a completed state.

FIG. 2B shows a pullout type sensor head 30B as one example of the sensor head 30 shown in FIG. 1 in an exploded manner. FIG. 6 shows a cross section of the sensor head 30B in a completed state. To facilitate the understanding of the sensor head 30B, in these drawings, constitutional elements which are identical with the constitutional elements shown in FIG. 2A are given same symbols. "Pullout-type" means that a liquid blocking film 81 which is to be pulled out at the time of using the sensor head 30B is interposed between a liquid retaining material 51 and electrodes 41, 42.

As can be clearly understood from FIG. 2B, in the same manner as the sensor head 30A shown in FIG. 2A, the sensor head 30B includes: a rectangular substrate 31 having a predetermined size; a first electrode 41 and a second electrode 42 having a circular disc shape or a circular columnar shape and arranged on a mounting surface 31a which constitutes one of main surfaces of the substrate 31 in a spaced-apart manner along one side 31c; and a first pullout electrode 43 and a second pullout electrode 44 extending in parallel to each other from the first and the second electrodes 41, 42 toward an opposite side (edge portion) 31e of the substrate 31.

The sensor head 30B further includes a liquid blocking film 81 having an approximately rectangular shape on the mounting surface 31a of the substrate 31. The liquid blocking film 81 is arranged so as to integrally cover the first electrode 41 and the second electrode 42. The liquid blocking film 81 covers an approximately ⅓ of the mounting surface 31a close to a side 31c of the substrate 31.

The liquid blocking film 81 is covered with a liquid retaining sheet 51. The liquid retaining sheet 51 covers approximately half region of the mounting surface 31a close to the side 31c of the substrate 31. In other words, the liquid blocking film 81 is arranged between the liquid retaining sheet 51 and the first electrode 41 and the second electrode 42.

A side 81c which is one of four sides of the liquid blocking film 81 is arranged at a position which coincides with the side 31c of the substrate 31 (that is, a side 71c of a sealing sheet 71) and hence, the side 81c is arranged at a position projecting outwardly (−X direction) from a side 51c of the liquid retaining sheet 51. That the liquid blocking film 81 has a projecting portion 81x which projects in the −X direction from a region where the liquid retaining sheet 51 is present. A tab 81g which projects in the −X direction is formed on the projecting portion 81x for facilitating the pulling out of the liquid blocking film 81. The projecting portion 81x is joined by adhesion to an edge portion of the sealing sheet 71 along a side 71c corresponding to the projecting portion 81x by way of a side 61c corresponding to the projecting portion 81x cut of four sides 61c, 61d, 61e, 61f of a double-sided adhesive tape 61 having a rectangular frame shape. That is, in the sensor head 30B, the edge portion of the sealing sheet 71 along the side 71c is not adhered to the mounting surface 31a but is adhered to the projecting portion 81x of the liquid blocking film 81.

Out of four sides of the liquid blocking film 81, two sides 81d, elf arranged adjacent to the side 61c are arranged at positions which coincide with two corresponding sides 51d, 51f of the liquid retaining sheet 51. Accordingly, two sides 81d, 81f are arranged at positions retracted inward from the sides 31d, 31f of the substrate 31 by a certain size (see FIG. 6)

Further, as shown in FIG. 28, out of four sides of the liquid blocking film 81, the remaining side 81e is arranged at a position retracted in the −X direction from the side 51e of the liquid retaining sheet 51. That is, the liquid retaining sheet 51 has an extending portion 51x extending in the +X direction beyond the liquid blocking film 81. The extending portion 51x is adhered to the mounting surface 31a by an adhesive agent not shown in the drawing (a double-sided adhesive tape also being used).

The liquid blocking film 81 is joined to none of the mounting surface 31a, the first electrode 41, the second electrode 42 and the liquid retaining sheet 51 by adhesion or the like.

In the sensor head 30B, as can be clearly understood from FIG. 6, the liquid blocking film 81 is arranged between the liquid retaining sheet 51 and the first electrode 41 and the second electrode 42. The liquid blocking film 81 is made of, for example, polyester, acrylic, polyethylene, polyimide resin (nylon), polypropylene, polyvinylchloride, aluminum foil or the like. The liquid blocking film 81 is a non-water permeable film and has a property of blocking permeation of liquids. Accordingly, the liquid blocking film 81 can prevent a drawback that the standard liquid impregnated into the liquid retaining sheet 51 is deteriorated due to contact with the first electrode 41 and the second electrode 42 over a long period. This brings about an advantageous effect that, for example, when the sensor head 30B is placed on a market as a commercially available product, it is possible to ensure a long period during which the sensor head 30B can be calibrated with high degree of accuracy using the standard liquid.

Particularly, when the first electrode 41 and the second electrode 42 contain an inner liquid for ion concentration measurement, the standard liquid impregnated into the liquid retaining sheet 51 and the inner liquid are blocked from each other by the liquid blocking film 81 and hence, the standard liquid and the inner liquid are not mixed with each other. Accordingly, it is unnecessary to take into account the mixing of these liquids and hence, it is possible to adopt inner liquids and the standard liquid optimum for the first electrode 41 and the second electrode 42.

The liquid blocking film 81 is expected to be removed by a user immediately before the sensor head 30B is used.

Figures 24, 25:
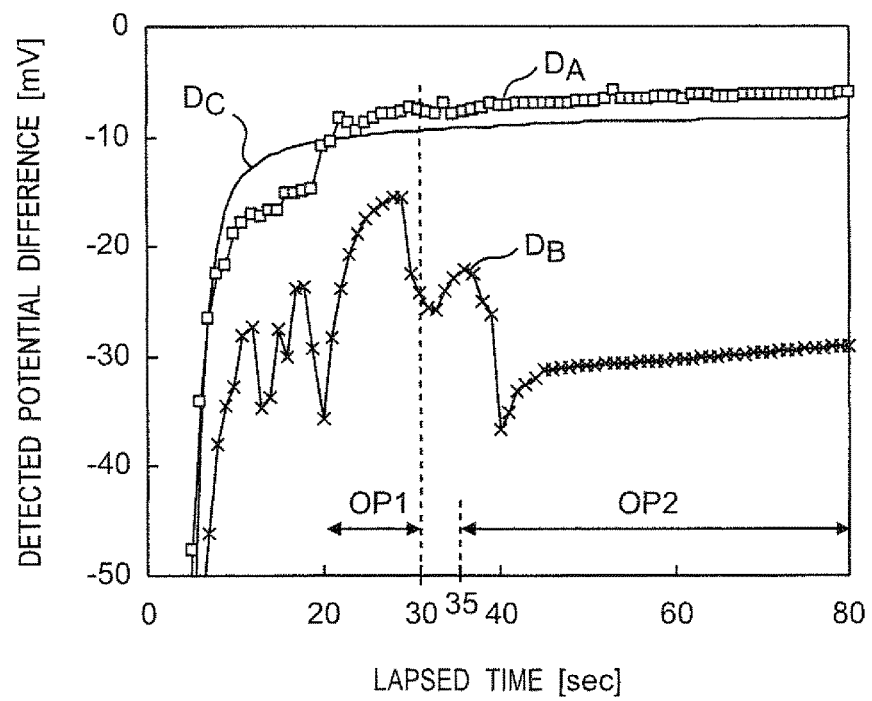
FIG. 24 is a graph showing a change in a detected potential with time when an NaCl aqueous solution is directly sprayed to the sensor head of the embodiment, a change in a detected potential with time when an NaCl aqueous solution is directly sprayed to a sensor head of a comparison example, and a change in a detected potential with time when the sensor head of the comparison example is immersed in an NaCl aqueous solution together.
FIG. 25 is a table showing the result obtained by analyzing the measured data shown in FIG. 24.

The projecting portion 81x of the liquid blocking film 81 shown in FIG. 25 is joined to the sealing sheet 71. Accordingly, in removing the sealing sheet 71 immediately before a user uses the sensor head 30A, the user is aware of the joining of the sealing sheet 71 with the liquid blocking film 81 by way of the projecting portion 81x, and is urged to pull out the liquid blocking film 81. In response to this, by pinching the projecting portion 81x or the tab 81g of the liquid blocking film 81 and the sealing sheet 71 immediately before the sensor head 305 is used, the user can pull out the liquid blocking film 81 in the −X direction along the mounting surface 31a from between the liquid retaining sheet 51 and the first and the second electrodes 41, 42. That is, by performing an operation of removing the sealing sheet 71 one time, the user can pull out the liquid blocking film 81 simultaneously. In this case, it is possible to prevent the user from forgetting pulling out the liquid blocking film 81.

The liquid retaining sheet 51 has an extending portion extending in the +X direction extending beyond the liquid blocking film 81 on the mounting surface 31a, and the extending portion is hermetically adhered to the mounting surface. Accordingly, when the liquid blocking film 81 is pulled out in the −X direction, the liquid retaining sheet 51 is not removed together with the liquid blocking film 81 and is brought into direct contact with the first electrode 41 and the second electrode 42. This brings about a state where the standard liquid exudes from the liquid retaining sheet 51 and is brought into contact with the first electrode 41 and the second electrode 42. By detecting a potential difference or an electric current between the first electrode 41 and the second electrode 42 in this state in the same manner as the contact-type sensor head 30A described previously, measured data can be obtained with high degree of accuracy with respect to the standard liquid. Then, calibration is performed using this measured data with respect to the standard liquid.

The pullout type sensor head 30B is provided by merely inserting the liquid blocking film 81 into the contact type sensor head 30A explained previously and hence, the number of constitutional elements is relatively small, thereby the sensor head 30B can be miniaturized and can be manufactured at a low cost.

FIG. 8, FIG. 10, FIG. 12 and FIG. 14 show various specific constitutional examples 30B-1, 30B-2, 30B-3 and 30B-4 of the pullout type sensor head 30B which respectively correspond to the constitutional examples 30A-1, 30A-2, 30A-3, 30A-4 shown in FIG. 7, FIG. 9, FIG. 11 and FIG. 13 explained previously.

The constitutional examples 30B-1, 30B-2, 30B-3 and 30B-4 shown in FIG. 8, FIG. 10, FIG. 12 and FIG. 14 are provided by merely inserting the liquid blocking film 81 into the constitutional examples 30A-1, 30A-2, 30A-3 and 30A-4 shown in FIG. 7, FIG. 9, FIG. 11 and FIG. 13, respectively. Accordingly, when a user pulls out the liquid blocking film 81 immediately before the constitutional examples 30B-1, 30B-2, 30B-3 and 30B-4 are used, the constitutional examples 30B-1, 30B-2, 30B-3 and 30B-4 are brought into the same state as the constitutional examples 30A-1, 30A-2, 30A-3 and 30A-4 shown in FIG. 7, FIG. 9, FIG. 11 and FIG. 13, respectively, and hence, the same measurement can be carried out.

(Verification Experiment 1)

In the verification experiment, inventors of the present invention have, with respect to various liquids to be measured, compared concentration measured values obtained by calibrating a commercially available sensor head (one-liquid calibration explained in the column "Background art" of the present specification) with concentration measured values obtained by calibrating a contact type sensor head according to the present invention (referred to as "embodiment sensor head" when appropriate).

i) Measurement Using a Commercially Available Sensor Head

As a commercially available ion sensor, a sodium ion sensor and a potassium ion sensor (a compact sodium ion meter C-122 type and a compact potassium ion meter C-131 type manufactured by Horiba, Ltd) were prepared. These commercially available ion sensors respectively include, as shown in FIG. 17A, a sensor head (hereinafter referred to as "commercially available sensor head" when appropriate) 130 and a body 110. The sensor head 130 includes: an ion selection electrode 141 having an ion selection film which selectively allows sodium ion (or potassium ion) contained in the liquid to be measured to permeate therethrough or to be absorbed therein; and a reference electrode 142 which is a non-sensitive electrode. The body 110 includes: a detection part 115 which obtains the concentration of sodium ion (or potassium ion) contained in the liquid to be measured based on an output from the sensor head 130; and a concentration display part 120 which displays the concentration obtained by the detection part 115.

The one-liquid calibration described previously was performed with respect to these commercially available sensor heads using respectively accompanied calibration liquids (for $Na^+$ concentration measurement, for $K^+$ concentration measurement).

As liquids to be measured, $N^+$ solutions having various concentrations (concentration range: 230 ppm to 4600 μm) were prepared using sodium chloride, and $K^+$ solutions having various concentrations (concentration range: 391 ppm to 7820 ppm) were prepared using potassium chloride.

Prepared Na⁺ solutions and K⁺ solutions having various concentrations were dropped on the sodium ion sensor and the potassium ion sensor, respectively, and concentration measured values displayed on the concentration display part 120 were recorded.

ii) Measurement by the Embodiment Sensor Head

In this embodiment, as the contact type sensor head according to the present invention, the embodiment sensor head (indicated by symbol 30A-1' in FIG. 17B) corresponding to the constitutional example 30A-1 in FIG. 7 was prepared as follows in a simple manner by making use of the commercially available sensor head 130 shown in FIG. 17A.

A filter paper (manufactured by MUNKTELL: type 389) which constitutes a material of the liquid retaining sheet 51 was arranged on the commercially available sensor head 130 such that the filter paper covers the ion selection electrode 141 and the reference electrode 142 integrally. A planar direction size of the filter paper was set equal to a planar direction size of a substrate of the commercially available sensor head 130. Only edge portions of the filter paper were adhered to the substrate of the commercially available sensor head 130 using a double-sided adhesive tape, and a center portion (a region inside the edge portion) of the filter paper was brought into direct contact with the ion selection electrode 141 and the reference electrode 142. A calibration liquid for Na⁺ concentration measurement (or K⁺ concentration measurement) accompanied with the ion sensor was dropped on the filter paper so as to impregnate the calibration liquid into the filter paper as the standard liquid. Thereby, a state was brought about where the calibration liquid exuded from the filter paper and was brought into contact with the ion selection electrode 141 and the reference electrode 142. A Parafilm (registered trademark) was used as a material of the sealing sheet 71, and the Parafilm was arranged so as to cover the whole sensor head substrate together with the ion selection electrode 141, the reference electrode 142 and the liquid retaining sheet 51. In this manner, the embodiment sensor heads 30A-1' for Na⁺ concentration measurement and K⁺ concentration measurement are prepared respectively.

With respect to the embodiment sensor heads 30A-1' for Na⁺ concentration measurement and K⁺ concentration measurement, one-point calibration was applied to a calibration liquid impregnated into the liquid retaining sheet 51 by making use of the body 110 (by operating the detection part 115) in a storage state where the embodiment sensor heads 30A-1' were still covered with the sealing sheet 71.

Na⁺ solutions and K⁺ solutions having various concentrations which were prepared in the above-mentioned i) were respectively dropped on the embodiment sensor heads 30A-1' for Na⁺ concentration measurement and K⁺ concentration measurement, and concentration measured values displayed on the concentration display part 120 were recorded.

ii) Result of Verification

Figure 20:
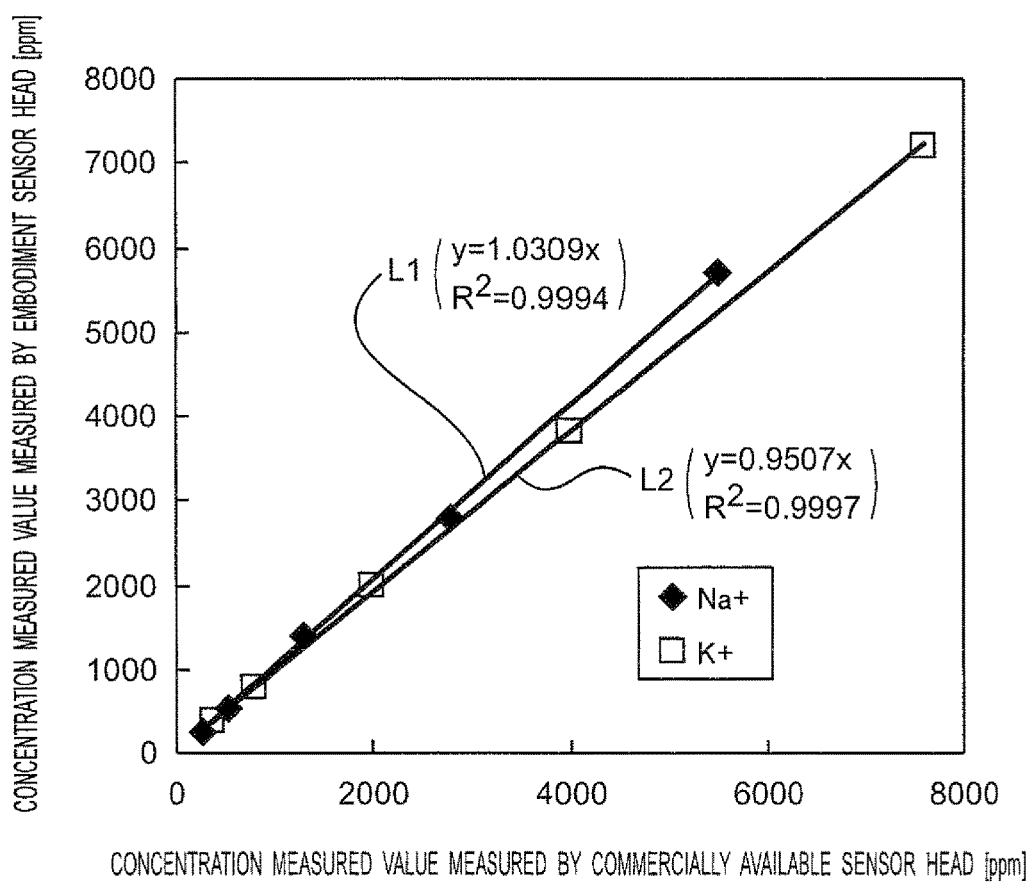
FIG. 20 is a graph showing a correlation between a result of measurement by a commercially available sensor head and a result of measurement by the sensor head of the embodiment with respect to various concentrations of specific components in a liquid to be measured.

FIG. 20 shows, with respect to various concentrations of Na⁺ in an Na⁺ solution as the liquid to be measured and various concentrations of K⁺ in a K⁺ solution as the liquid to be measured, correlations between concentration measured values (axis of abscissa x) measured by the commercially available sensor head 130 and concentration measured values (axis of ordinate y) measured by the embodiment sensor head 30A-1'. In the drawing, each black diamond mark ◆ indicates measured point with respect to Na⁺. With respect to Na⁺, the correlation is expressed by the formula y=1.0309x in linear approximation (L1), and the dispersion is 0.9994 ($R^2$=0.9994). In the drawing, each white square mark ☐ indicates measured point with respect to K⁺. With respect to K⁺, the correlation is expressed by the formula y=0.9507x in linear approximation (L2), and the dispersion is 0.9997 ($R^2$=0.9997).

In this manner, it was confirmed that there is extremely favorable correlation between the concentration measured value measured by the commercially available sensor head 130 (axis of abscissa x) and the concentration measured value measured by the embodiment sensor head 30A-1' (axis of ordinate y). Accordingly, it was found that the embodiment sensor head 30A-1' can also acquire the accuracy in measurement comparable to the accuracy in measurement acquired by the commercially available sensor head 130.

(Verification Experiment 2)

An embodiment sensor head (indicated by symbol 30A-4') corresponding to the constitutional example 30A-4 shown in FIG. 13 was prepared as the contact type sensor head according to the present invention, and a concentration ratio between ions different from each other and contained in the liquid to be measured (composition being known) was measured.

i) Preparation of Embodiment Sensor Head

Figure 19B:
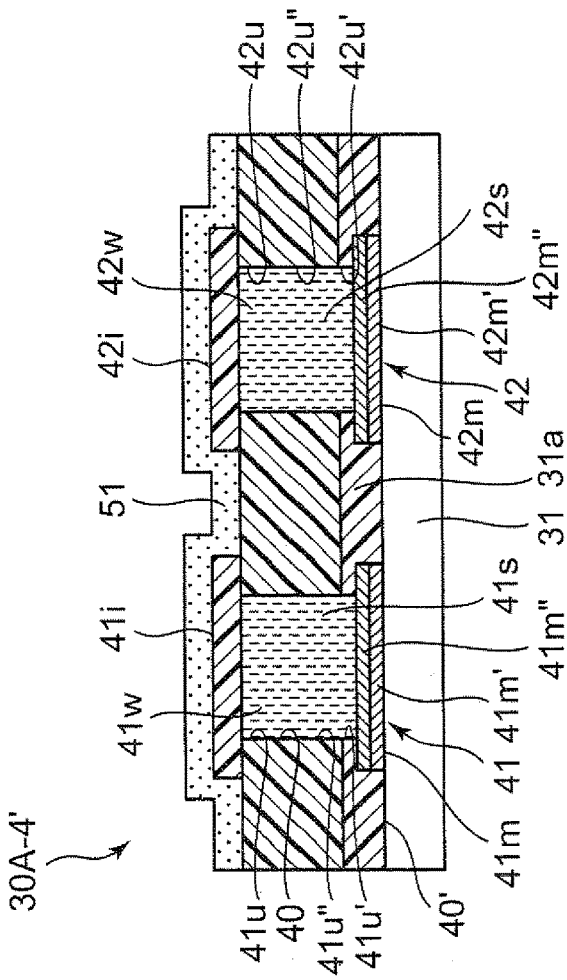
FIG. 19B is a cross-sectional view showing a constitution of the sensor head in a completed state corresponding to FIG. 19A.
Figure 19A:
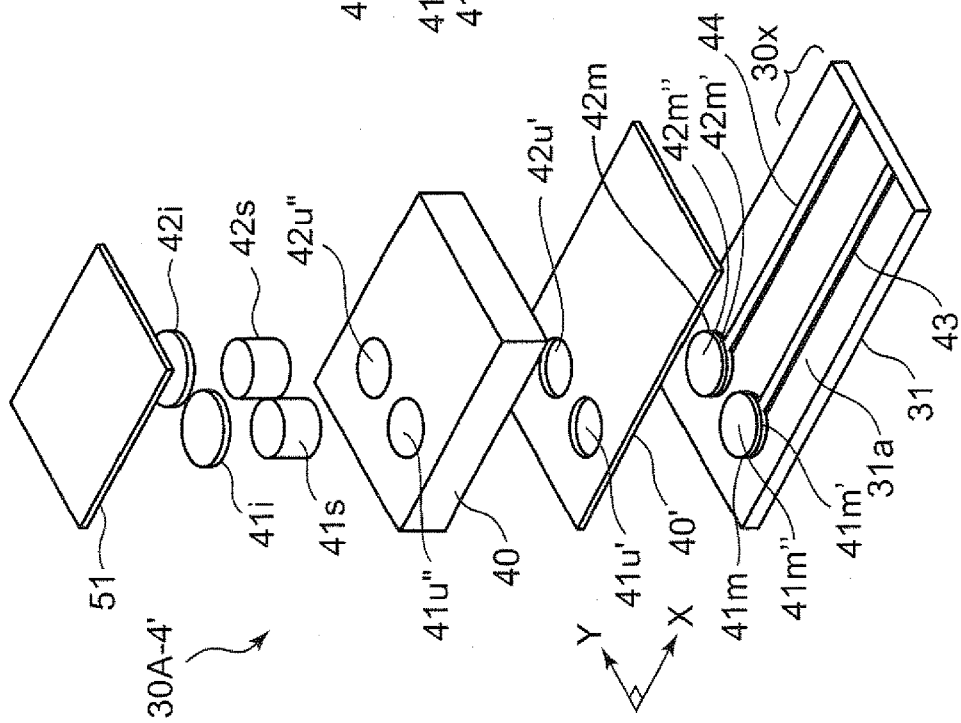
FIG. 19A is an exploded view of a contact type sensor head used in verification experiment.

FIG. 19A shows the embodiment sensor head 30A-4' which was prepared as a contact type sensor head according to the present invention in an exploded manner. FIG. 19B shows a cross section of the embodiment sensor head 30A-4' in a completed state.

Firstly, as shown in FIG. 19A, for forming the first electrode 41 and the second electrode 42, an Ag paste was applied to a main surface of a PET substrate by printing using a screen printing method so as to form a first core material lower layer 41m', a second core material lower layer 42m' a first pullout electrode 43 and a second pullout electrode 44. The first core material lower layer 41m' and the second core material lower layer 42m' were respectively formed by patterning with a diameter of 7 mm. The first pullout electrode 43 and the second pullout electrode 44 were respectively formed by patterning with an X-direction size of 40 mm and a Y-direction size of 1.5 mm, and a distance between the first pullout electrode 43 and the second pullout electrode 44 was set to 10 mm. The PET substrate was cut in an X-direction size of 50 mm and a Y-direction size of 20 mm, thus forming a rectangular substrate 31 shown in the drawing.

Next, an AgCl paste was printed using a screen printing method, thus forming a first core material upper layer 41m'' and a second core material upper layer 42m'' on the first core material lower layer 41m' and the second core material lower layer 42m'. The first core material upper layer 41m'' and the second core material upper layer 42m'' had a diameter of 7 mm equal to the diameter of the first core material lower layer 41m' and the second core material lower layer 42m'. Thereby, the first core material 41m and the second core material 42m were formed as inner electrodes.

To the substrate 21 as insulation base materials, a double-sided film base material 40' manufactured by 3M (X-direction size: 40 mm, Y-direction size: 20 mm, thickness: 0.05 mm) in which through holes (diameter: 4 mm) 41u', 42u' concentric with patterns of the first core material 41m and the second core material 42m had been formed, and a strong double-sided tape 40 (X-direction size: 10 mm, Y-direction size: 20 mm, thickness: 0.33 mm) made of a PET substrate/acrylic adhesive agent in which similar through holes (diameter: 4 mm) 41u''', 42u''' had been formed were adhered. Thereby, an insulation layer for insulating the first core material 41m, the second core material 42m, and the first envelope 41u and the second envelope 42U which constitute liquid reservoirs were formed (see FIG. 19B).

Next, into the inside of first envelope 41u and a second envelope 42u, the same mixed liquid made of sodium chloride and potassium chloride (concentration ratio $M_{ref\_b}$ between sodium ion and potassium ion being known) was dropped as the first inner liquid 41s and the second inner liquid 42s respectively.

Next, a sodium ion selection film and a potassium ion selection film were prepared by a known method (for example, see DOJINDO LABORATORIES "P-37, measure ion concentration using electrodes", searched on Jul. 15, 2011, Internet <URL: http://www.dojindo.co.jo/technical/protocol/p37.pdf>. The sodium ion selection film and the potassium ion selection film were cut in a circular shape with a diameter of 6 mm respectively, thus forming the first ion selection film 41i and the second ion selection film 42i. These first ion selection-film 41i and second ion selection film 42i were adhered and fixed to the double-sided tape 40 such that the first ion selection film 41i and the second ion selection film 42i covered the first window portion 41w and the second window portion 42w of the first envelope 41u and the second envelope 42u.

A Kimwipe (registered trademark owned by NIPPON PAPER CRECIA Co., LTD.) was cut so as to form a liquid retaining sheet 51 having an X-direction size of 10 mm and a Y-direction size of 20 mm and was adhered thereto such that the liquid retaining sheet 51 integrally covered the first electrode 41 and the second electrode 42.

The same mixed liquid used as the first inner liquid 41s and the second inner liquid 42s as the standard liquid was dropped on the liquid retaining sheet 51 and was impregnated into the liquid retaining sheet 51.

As the last step, all of the first electrode 41, the second electrode 42, the liquid retaining sheet 51 and the substrate 31 were hermetically sealed using a vacuum pack made of a Parafilm (registered trademark) which constituted a sealing member 71 (the vacuum pack not shown in FIG. 19A and FIG. 19B for the sake of brevity). In this manner, the embodiment sensor head 30A-4' was prepared.

ii) Constitution of Measurement System

Figure 18B:
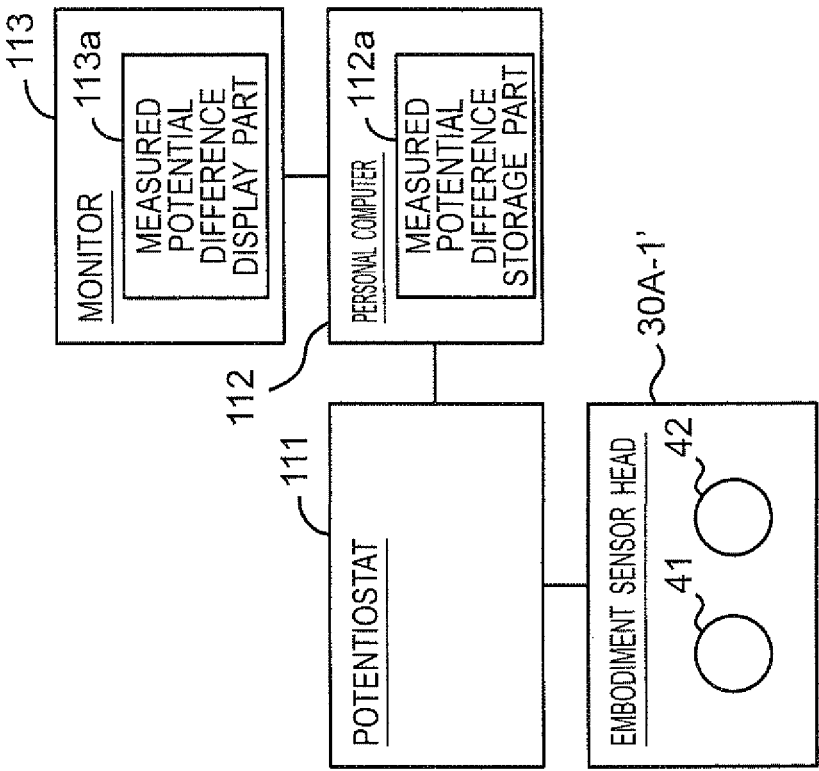
FIG. 18A and FIG. 18B are block diagrams respectively showing a constitution of a measurement system used in verification experiments carried out for respective sensor heads.
Figure 18A:
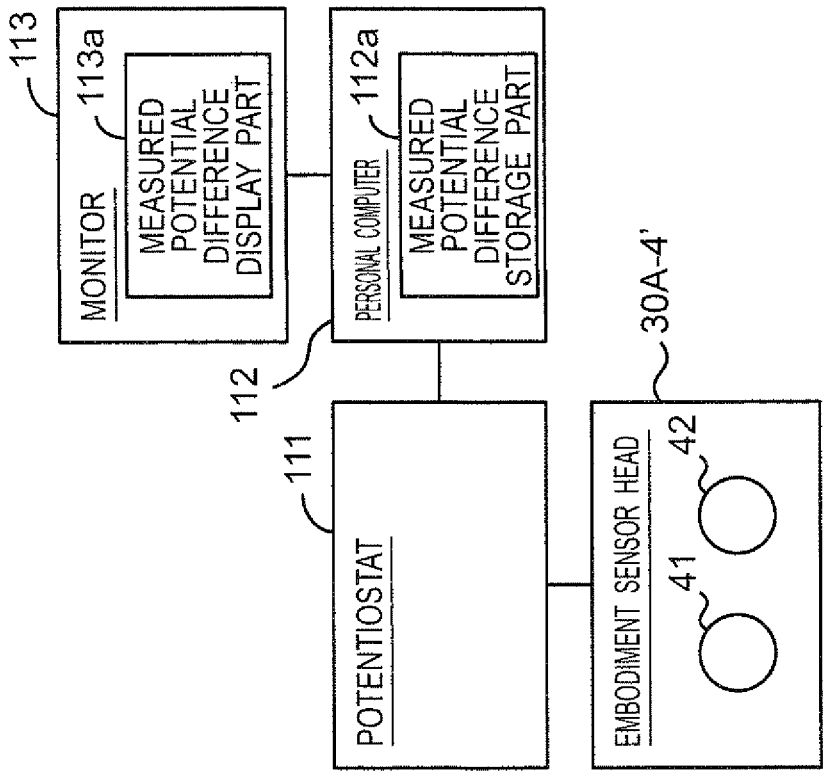

FIG. 18A shows a constitution of a measurement system including the embodiment sensor head 30A-4'. A vacuum pack which constituted the sealing member 71 was removed from the embodiment sensor head 30A-4' immediately before the measurement system was constituted.

The measurement system included: a commercially available potentiostat (manufactured by HOKUTO DENKO CORP.: HZ-5000) 111 which was connected to the embodiment sensor head 30A-4'; a personal computer 112 which receives an output from the potentiostat 111, and a monitor 113 connected to the personal computer 112.

The potentiostat 111 detects a potential difference between the first electrode 41 and the second electrode 42 of the embodiment sensor head 30A-4' and outputs a signal indicative of the detected potential difference.

The personal computer 112 included a measured potential difference recording part 112a. The personal computer 112 makes the measured potential difference recording part 112a store a detected potential difference which the potentiostat 111 outputs, and outputs a signal indicative of the detected potential difference to the monitor 113 in real time.

The monitor 113 includes a measured potential display part 113a, and displays the detected potential difference by the measured potential display part 113a in real time.

iii) Measurement with Respect to Standard Liquid

Measured data (potential difference $E_{ref\_b}$ [mV]) with respect to the standard liquid impregnated into the liquid retaining sheet 51 of the embodiment sensor head 30A-4' was obtained by the measurement system, and the measured data was recorded in the measured potential difference recording part 112a.

iv) Measurement with Respect to Liquid to be Measured

Four kinds of liquids to be measured were prepared while setting in a variable manner a concentration ratio between sodium ion and potassium ion (Na[ppm]/K[ppm]) (concentration ratio being referred to as "set concentration ratio"). These liquids to be measured were directly sprayed to the liquid retaining sheet 51 of the embodiment sensor head 30A-4', measured data (potential difference $E_{s\_b}$ [mV]) was obtained with respect to the liquids to be measured, and the measured data were recorded in the measured potential difference recording part 112a.

Thereafter, using the concentration ratio $M_{ref\_b}$ and the potential difference $E_{ref\_b}$ [mV] with respect to the standard liquid and the potential difference $E_{s\_b}$ [mV] with respect to the liquid to be measured, the concentration ratio $M_{s\_b}$ with respect to the liquid to be measured (this concentration ratio being referred to as "measured concentration ratio") was obtained by the previously mentioned formula (8).

v) Result of Verification

Figure 21:
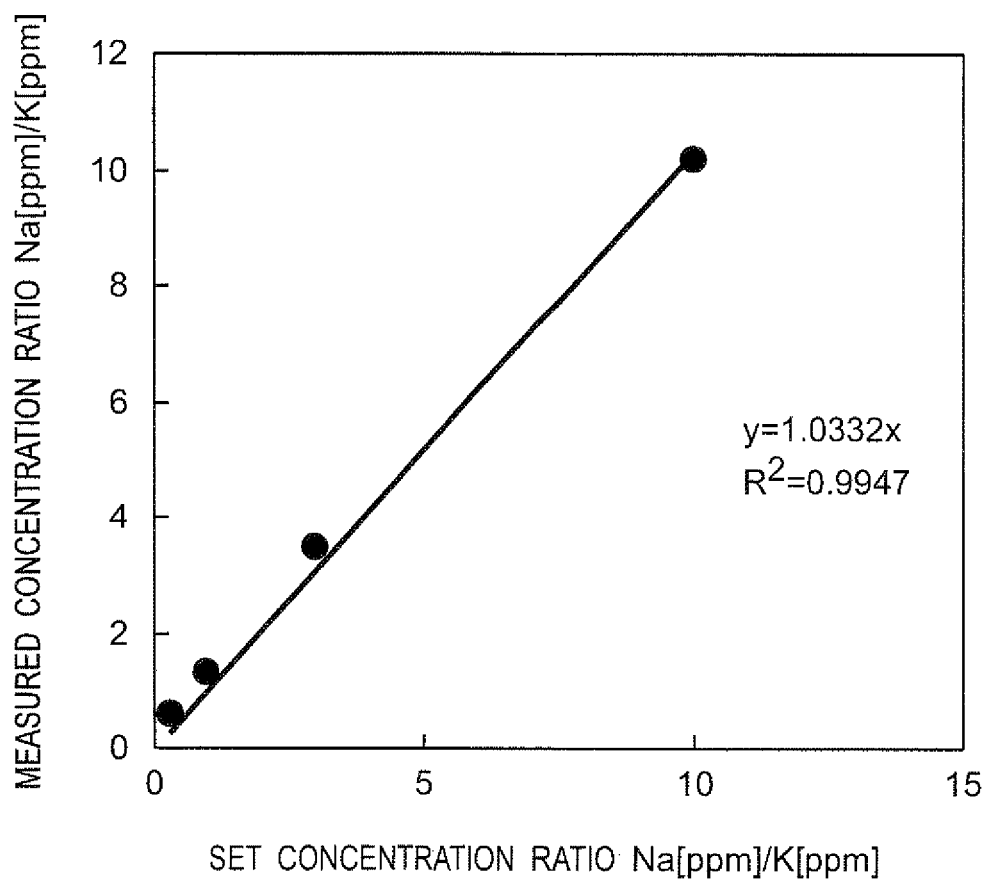
FIG. 21 is a graph showing a result of measurement by the sensor head of the embodiment when a concentration ratio between a first specific component and a second specific component in a liquid to be measured is varied.

FIG. 21 shows a correlation between set concentration ratios (axis of abscissa x) and measured concentration ratios (axis of ordinate y) with respect to the above-mentioned four kinds of liquids to be measured. A solid circular black mark ● in the drawing indicates measured points. As a result, the correlation is expressed by the formula y=1.0332x in linear approximation, and the dispersion is 0.9947 ($R^2$=0.9947).

In this manner, it was confirmed that there is extremely favorable correlation between the set concentration ratios (axis of abscissa x) and the measured concentration ratios (axis of ordinate y) with respect to liquids to be measured. Accordingly, it was found that with the use of the embodiment sensor head 30A-4', the favorable accuracy in measurement can be acquired with respect to the concentration ratio between ion species different from each other.

(Verification Experiment 3)

Reproducibility of measured data with respect to the liquid to be measured was evaluated using a contact type sensor head according to the present invention.

i) Constitution of Embodiment Sensor Head and Measurement System

As the contact type sensor head according to the present invention, the embodiment sensor head 30A-1' shown in FIG. 17B which was prepared in the verification experiment 1 was used. However, in this experiment, a Kimwipe (area: approximately 1 $cm^2$) was used in place of the filter paper as a material of the liquid retaining sheet 51, and a sodium chloride aqueous solution liquid was impregnated into the Kimwipe as the standard liquid.

A measurement system included, as shown in FIG. 182, a commercially available potentiostat 111, a personal computer 112 and a monitor 113.

ii) Measurement with Respect to Standard Liquid

Measured data (potential difference $E_{ref}$ [mV]) with respect to the standard liquid impregnated into the liquid retaining sheet 51 of the embodiment sensor head 30A-1' was obtained by the measurement system, and a reference potential $E_0$ for calibration was calculated based on the measured data. Based on the result of calculation, calibration detected potential difference was performed with respect to liquids to be measured described hereinafter.

iii) Measurement with Respect to Liquid to be Measured

Three kinds of liquids to be measured were prepared by dissolving sodium chloride in pure water and by changing NaCl concentration (the concentration being hereinafter referred to as "set NaCl concentration"). The set NaCl concentrations were 10 [mM/L], 100 [mM/L] and 500 [mM/L].

Next, the mounting surface 31a of the embodiment sensor head 30A-1' (accordingly, the liquid retaining sheet 51) was fixed to a stand at an angle of 45 degrees in a downwardly inclined manner. In this state, the inventor started observation of a potential difference (natural potential) between the ion selection electrode 41 and the reference electrode 42 using the potentiostat 111 and the personal computer 112.

The inventor performed the following operations while observing the potential difference.

a) 5 mL of NaCl aqueous solution having the set NaCl concentration 100 [mM/L] was directly sprayed to the liquid retaining sheet 51 for approximately 5 seconds using a pipetman.

b) Subsequently, spraying was interrupted for 60 seconds.

c) Then, 5 mL of NaCl aqueous solution having the set NaCl concentration 10 [mM/L] was directly sprayed to the liquid retaining sheet 51 for approximately 5 seconds using a pipetman.

d) Subsequently, spraying was interrupted for 60 seconds.

e) Then, 5 mL of NaCl aqueous solution having the set NaCl concentration 500 [mM/L] was directly sprayed to the liquid retaining sheet 51 for approximately 5 seconds using a pipetman.

f) Subsequently, spraying was interrupted for 60 seconds.

Such a series of operations a) to f) was continuously repeated 4 times.

iv) Result of Verification

Figure 22:
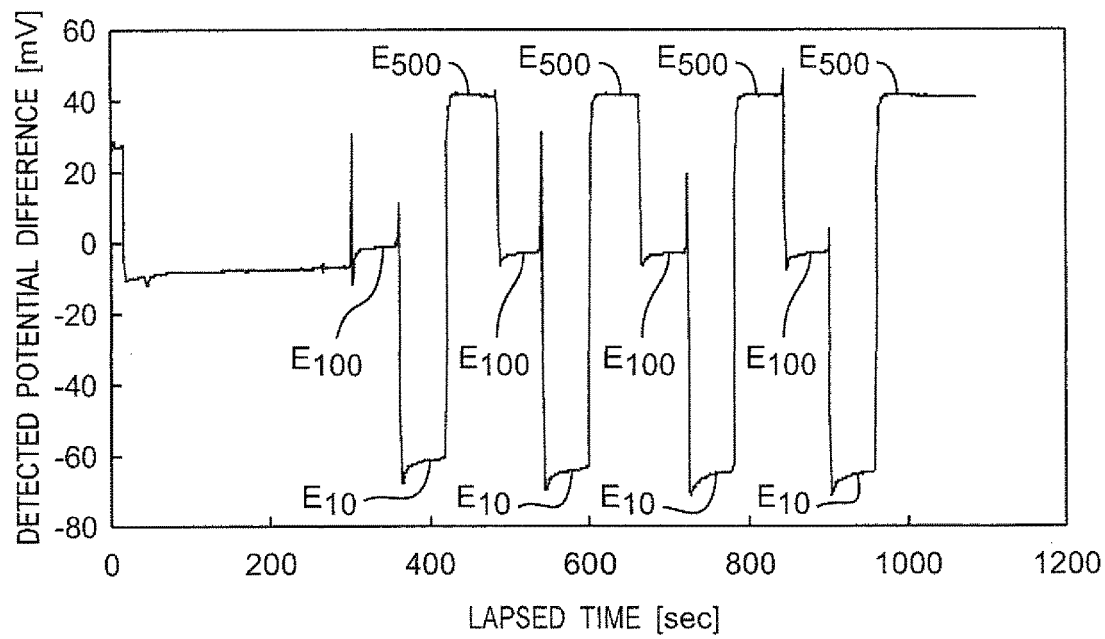
FIG. 22 is a graph showing a change in detected potential difference with time when three kinds of NaCl aqueous solutions having different concentrations of a liquid to be measured are repeatedly sprayed to the sensor head of the embodiment.

FIG. 22 shows a change in detected potential difference with time when three kinds of NaCl aqueous solutions having different concentrations which constitute liquids to be measured were repeatedly sprayed to the embodiment sensor head 30A-1'. In the drawing, symbol $E_{100}$ indicates a position where the above-mentioned operation a) was performed (spraying of the NaCl aqueous solution having the set NaCl concentration 100 [mM/L]), symbol $E_{10}$ indicates a position where the above-mentioned operation c) was performed (spraying of the NaCl aqueous solution having the set NaCl concentration 10 [mM/L]), and symbol $E_{500}$ indicates a position where the above-mentioned operation e) was performed (spraying of the NaCl aqueous solution having the set NaCl concentration 500 [mM/L]).

Figure 23:
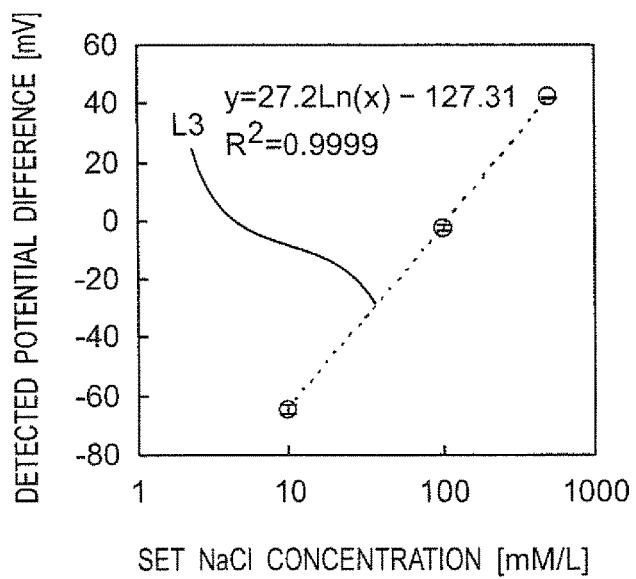
FIG. 23 is a graph showing a correlation between a set NaCl concentration and a detected potential difference obtained using the measured data shown in FIG. 22.

In the step of continuously repeating the series of operations a) to f) 4 times, the detected potential difference at a point of time after 20 seconds elapse from starting of each operation a), c), e) was recorded in the measured potential difference recording part 112a. FIG. 23 shows the correlation between the respective set NaCl concentrations (axis of abscissa x) and the respective recorded detected potential differences (axis of ordinate y).

Then, an average value and a standard deviation of the detected potential differences were calculated with respect to each set NaCl concentration. As a result, a CV value (standard deviation/average value) at each set NaCl concentration was 3.1% or less. This dispersion in measurement was substantially equal to that in measurement of the commercially available sensor head 130. Further, the dispersion of a calibration curve L3 (approximation formula y=27.2Ln(x) 127.31) obtained by linear approximation on a semilogarithmic graph became an extremely high value of 0.9999 ($R^2$=0.9999).

Accordingly, it was confirmed that, with the use of the embodiment sensor head 30A-1', measurement with high reproducibility can be achieved even when the liquid retaining sheet 51 is not peeled off each time of measurement of the set NaCl concentration.

In this verification experiment, a front surface area of the Kimwipe used as the liquid retaining sheet 51 was approximately 1 $cm^2$. A spray amount per one time of the liquid to be measured (NaCl aqueous solution) having each set NaCl concentration was 5 mL. As a result of the experiment, it was confirmed that, as a quantity of the liquid to be measured which is to be sprayed to the liquid retaining sheet 51, it is sufficient to spray 5 mL per 1 $cm^2$ of the front surface area of the liquid retaining sheet 51.

(Verification Experiment 4)

The reliability and a response speed of measured data were evaluated with respect to the liquid to be measured using a contact type sensor head according to the present invention.

i) Constitution of Embodiment Sensor Head and Measurement System

As the contact type sensor head according to the present invention, the embodiment sensor head 30A-1' and the measurement system which were prepared in the verification experiment 3 were used (see FIG. 18B).

ii) Measurement with Respect to Standard Liquid

In the above-mentioned measurement system, measurement was started from a state where the standard liquid was impregnated into the liquid retaining sheet 51 of the embodiment sensor head 30A-1'.

iii) Measurement with Respect to Liquid to be Measured

As the liquid to be measured, an NaCl aqueous solution having the set NaCl concentration 100 [mM/L] was prepared by dissolving sodium chloride in pure water.

Next, in the same manner as the verification experiment 3, the mounting surface 31a of the embodiment sensor head 30A-1' (accordingly, the liquid retaining sheet 51) was fixed to a stand at an angle of 45 degrees in a downwardly inclined manner. In this state, the inventor started the observation of a potential difference (natural potential) between the ion selection electrode 41 and the reference electrode 42 using the potentiostat 111 and the personal computer 112.

The inventor performed the following operations while observing the potential difference.

a) An NaCl aqueous solution having the set NaCl concentration 100 [mM/L] was directly sprayed to the liquid retaining sheet 51 at a rate of approximately 1 mL per 1 second for 30 seconds using a wash-bottle.

b) Next, the spraying of the NaCl aqueous solution was stopped, and the potential difference was observed for 50 seconds. The potential difference which was obtained with respect to the NaCl aqueous solution which constitutes the liquid to be measured by the operations a), b) using the embodiment sensor head 30A-1' is referred to as "measured data $D_A$".

c) Thereafter, the liquid retaining sheet 51 was peeled off from the embodiment sensor head 30A-1' (the sensor head in such a state being referred to as "comparison example sensor head 30A-1"). An NaCl aqueous solution having the set NaCl concentration 100 [mM/L] was directly sprayed to an ion selection electrode 41 and a reference electrode 42 of the comparison example sensor head 30A-1" at a rate of approximately 1 mL per 1 second for 30 seconds using the wash-bottle.

d) Subsequently, the spraying of the NaCl aqueous solution was stopped, and the potential difference was observed for 50 seconds. The potential difference obtained with respect to the NaCl aqueous solution which constituted the liquid to be measured by the operations c), d) using the comparison example sensor head 30A-1" is referred to as "measured data $D_B$".

e) Thereafter, the comparison example sensor head 30A-1" was immersed in an NaCl aqueous solution having the set NaCl concentration 100 [mM/Cl] and stored in a beaker for 80 seconds. The potential difference obtained with respect to the NaCl aqueous solution which constituted the liquid to be measured by the operation e) using the comparison example sensor head 30A-1" is referred to as "measured data $D_C$".

iv) Result of Verification

FIG. 24 shows together a measured data $D_A$ from the point of time that the operation a) was started, a measured data $D_B$ from the point of time that the operation c) was started, and the measured data $D_C$ from the point of time that the operation e) was started. In FIG. 24, an abscissa expresses a lapsed time [sec] where the point of time that each operation was started is used as the reference time (time: 0), and an ordinate expresses a detected potential difference [mV]. Assuming as OP1 a period from a point of time that 20 seconds have elapsed to a point of time that 30 seconds have elapsed, and assuming as OP2 a period from a point of time that 35 seconds have elapsed to a point of time that 80 seconds have elapsed, Table in FIG. 25 shows that the result of calculating standard deviations σ [mV] of the detected potential differences indicated by the measured data $D_A$, $D_B$, $D_C$ for the periods OP1, OP2. In columns (A), (B), (C) in the Table, conditions under which the measured data $D_A$, $D_B$, $D_C$ were observed are described.

From FIG. 24, it is found that the measured data $D_B$ obtained by direct spraying using the comparison example sensor head 30A-1" was unstable. To the contrary, it is found that the measured data $D_A$ obtained by direct spraying using the embodiment sensor head 30A-1' and the measured data $D_C$ obtained by immersion using the comparison example sensor head 30A-1" change in a stable manner. Actually, as shown in column (B) in FIG. 25, with respect to the measured data $D_B$ obtained using the comparison example sensor head 30A-1", the standard deviation of the detected potential difference during the period OP1 (during spraying the liquid to be measured) was large, that is, 6.02 [mV] (σ=6.02 [mV]). To the contrary, in the column (A) shown in FIG. 25, with respect to the measured data $D_A$ obtained by direct spraying using the embodiment sensor head 30A-1', the standard deviation of the detected potential difference during the period OP1 was small, that is, 1.06. [mV] (σ=1.06 [mV]). Further, in the column (C) shown in FIG. 25, with respect to the measured data $D_C$ obtained by immersion using the comparison example sensor head 30A-1", the standard deviation of the detected potential difference during the period OP1 was small, that is, 0.29 [mV] (σ=0.29 [mV]).

With respect to the measured data $D_B$ obtained by direct spraying using the comparison example sensor head 30A-1", it is found that the detected potential difference during the period OP2 (after stopping spraying) largely differs from the detected potential difference of the measured data $D_C$ obtained by immersion during the period OP2 so that the comparison example sensor head 30A-1" lacks reliability. The reason is considered that the liquid retaining sheet 51 was removed in the comparison example sensor head 30A-1" and hence, the liquid to be measured could not be held on a surface of the ion selection electrode 41 and a surface of the reference electrode 42. To the contrary, with respect to the measured data $D_A$ obtained by direct spraying using the embodiment sensor head 30A-1', it is found that the detected potential difference during the period OP2 is approximately equal to the detected potential difference of the measured data $D_C$ obtained by immersion during the period OP2 so that the embodiment sensor head 30A-1' has reliability. Particularly, it is found that even when the embodiment sensor head 30A-1' takes a downwardly inclined posture, the reliability of measured data is ensured.

In a lower column of Table shown in FIG. 25, a time which the detected potential differences respectively reach 90% of saturated values from the above-mentioned reference time (referred to as "90% response time") is indicated with respect to the measured data $D_A$ obtained by direct spraying using the embodiment sensor head 30A-1' and the measured data $D_C$ obtained by immersion using the comparison example sensor head 30A-1". As shown in the column, the 90% response time of measured data $D_A$ was 29 [sec], and the 90% response time of measured data $D_C$ was 25 [sec]. Accordingly, it is confirmed that there is almost no difference between both measured data.

From the above, it is confirmed that measured data $D_A$ obtained by direct spraying using the embodiment sensor head 30A-1' has reliability and also has a sufficiently high response speed.

Although the cases where the concentration or the concentration ratio of sodium ion or potassium ion was measured has been mainly explained in conjunction with several embodiments heretofore, the present invention is not limited to such cases. With the use of sensor head and the electrochemical sensor provided with such a sensor head according to the present invention, besides sodium ion and potassium ion, it is possible to measure the ion concentration or the ion concentration ratio of various ions such as calcium ion, chloride ion, lithium ion, nitric acid ion, nitrite ion, sulfuric acid ion, sulfite ion, iodide ion, magnesium ion, bromide ion, hyperchloride ion, hydrogen ion.

The sensor head and the electrochemical sensor according to the present invention are not limited to the embodiments exemplified above and can be modified in various ways.

INDUSTRIAL APPLICABILITY

The sensor head and the electrochemical sensor according to the present invention are applicable to various usages. For example, the electrochemical sensor according to the present invention can be used as an ion sensor for measuring sodium ion, potassium ion or chloride ion in blood or urine or an enzyme sensor for measuring creatinine, glucose or the like in the field of a biochemical test and a clinical laboratory test. Further, the electrochemical sensor according to the present invention can be used as a sensor for measuring pH in properties of water, a gas sensor for measuring dissolved oxygen, a nitric acid ion sensor for measuring nitric acid ion in soil or a gas sensor for measuring the concentration of ammonium or carbon dioxide in a gaseous phase in the field of environment measurement. Further, the electrochemical sensor according to the present invention can be used as a sensor for measuring pH in foods in the field of a food test.

The method of using an electrochemical sensor according to the present invention can be used for using an electrochemical sensor used in such various usages.

DESCRIPTION OF REFERENCE SIGNS

10: body
21: connector
30, 30A, 30B: sensor head
41: first electrode
42: second electrode
43: first pullout electrode 44: second pullout electrode
51: liquid retaining sheet
71: sealing sheet
72: sealing pack
81: liquid blocking film
90: electrochemical sensor

The invention claimed is:

1. A packaged sensor head for performing electrochemical measurement, comprising:
a mounting surface having insulation property;
a first electrode and a second electrode arranged on the mounting surface in a spaced-apart manner from each other;
a liquid retaining material arranged on the mounting surface in a state where the liquid retaining material covers the first electrode and the second electrode integrally, wherein the liquid retaining material is provided in the form of a sheet, and the liquid retaining material has liquid permeation properties that allow a liquid to be measured to permeate the liquid retaining material provided in a form of a sheet toward the first electrode and the second electrode, and wherein the liquid retaining material is impregnated with a standard liquid that is used as a reference in the electrochemical measurement;
a liquid blocking film which blocks permeation of the liquid, the liquid blocking film being removably arranged between the liquid retaining material and the first and second electrodes, wherein the first electrode includes a first core material having electric conductivity, a first envelope surrounding the first core material and having insulation property, and a first inner liquid for measurement of ion concentration which is filled between the first envelope and the first core material,
the second electrode includes a second core material having electric conductivity, a second envelope surrounding the second core material and having insulation property, and a second inner liquid for measurement of ion concentration which is filled between the second envelope and the second core material, and
a first window portion and a second window portion which are capable of allowing a contact between the first inner liquid, the second inner liquid and the standard liquid or the liquid to be measured are respectively formed on a surface of the first envelope and a surface of the second envelope which face the liquid retaining material in an opposed manner.

2. The packaged sensor head according to claim 1, wherein the mounting surface is one main surface of a substrate having a predetermined size, and
a first pullout electrode and a second pullout electrode which respectively extend from the first and the second electrodes toward an edge portion of the substrate on the mounting surface are provided to the mounting surface.

3. An electrochemical sensor comprising:
a packaged sensor head according to claim 1; and
a detection part which detects a potential difference or an electric current between the first electrode and the second electrode.

4. The packaged sensor head according to claim 1, further comprising a sealing member that covers at least the liquid retaining material for preventing a change in the standard liquid impregnated into the liquid retaining material.

5. The packaged sensor head according to claim 4, wherein:
the sealing member is provided as a sealing sheet and includes an edge portion,
the sealing member has a planar-direction size that is larger than a planar-direction size of the liquid retaining material, and
the edge portion of the sealing member is configured to adhere to the mounting surface.

6. The packaged sensor head according to claim 4, wherein:
the sealing member is provided as a bag, and
the sealing member covers a whole or a portion of a substrate forming the mounting surface, the first electrode, the second electrode, and the liquid retaining material.

7. The packaged sensor head according to claim 1, wherein the liquid retaining material has resistance to the standard liquid.

8. A method for using an electrochemical sensor which uses an electrochemical sensor which includes a packaged sensor head for performing electrochemical measurement and a detection part which detects a potential difference or an electric current in the sensor head,
the packaged sensor head comprising:
a mounting surface having insulation properties;
a first electrode and a second electrode arranged on the mounting surface in a spaced-apart manner from each other;
a liquid retaining material arranged on the mounting surface in a state where the liquid retaining material covers the first electrode and the second electrode integrally, wherein the liquid retaining material is impregnated with a standard liquid that is used as a reference in the electrochemical measurement; and
a liquid blocking film that blocks permeation of the liquid, the liquid blocking film being removably arranged between the liquid retaining material and the first and the second electrodes;
the method comprising the steps of:
detecting the potential difference or the electric current between the first electrode and the second electrode with respect to the standard liquid by pulling out the liquid blocking film from between the liquid retaining material and the first and second electrodes so as to bring the liquid retaining material into contact with the first electrode and the second electrode and operating the detection part; and
subsequently detecting the potential difference or the electric current between the first electrode and the second electrode with respect to the liquid to be measured by operating the detection part in a state where the standard liquid in the liquid retaining material is replaced with the liquid to be measured by spraying the liquid to be measured to the liquid retaining material or by immersing the liquid retaining material into the liquid to be measured.

* * * * *